US006541037B1

(12) United States Patent
Lee et al.

(10) Patent No.: US 6,541,037 B1
(45) Date of Patent: *Apr. 1, 2003

(54) DELIVERY VEHICLE

(75) Inventors: Dosuk D. Lee, Brookline, MA (US); Christian Rey, Castanet (FR); Maria Aiolova, Brookline, MA (US)

(73) Assignee: Etex Corporation, Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/729,342

(22) Filed: Oct. 16, 1996

Related U.S. Application Data

(63) Continuation-in-part of application No. 08/650,764, filed on May 20, 1996, now Pat. No. 6,214,368, which is a continuation-in-part of application No. 08/446,182, filed on May 19, 1995, now Pat. No. 5,676,976.

(51) Int. Cl.$^7$ .................. A61K 33/42; A61K 38/00; C01B 25/26
(52) U.S. Cl. .................. 424/602; 423/308; 423/311; 514/2
(58) Field of Search .................. 424/602; 514/2; 423/308, 311

(56) References Cited

U.S. PATENT DOCUMENTS

| | | | |
|---|---|---|---|
| 4,157,378 A | 6/1979 | Tomlinson et al. | 423/301 |
| 4,346,709 A | 8/1982 | Schmitt | 128/260 |
| 4,347,234 A | 8/1982 | Wahlig et al. | 424/15 |
| 4,429,691 A | 2/1984 | Niwa et al. | 128/92 C |
| 4,612,053 A | 9/1986 | Brown et al. | 706/35 |
| 4,684,673 A | 8/1987 | Adachi | 523/116 |
| 4,737,411 A | 4/1988 | Graves, Jr. et al. | 428/403 |
| 4,842,603 A | 6/1989 | Draenert | 623/16 |
| 4,849,193 A | 7/1989 | Palmer et al. | 423/308 |
| 4,880,610 A | 11/1989 | Constantz | 423/305 |
| RE33,161 E | 2/1990 | Brown et al. | 423/308 |
| 4,917,702 A | 4/1990 | Scheicher et al. | 623/16 |
| RE33,221 E | 5/1990 | Brown et al. | 423/308 |
| 4,938,938 A | 7/1990 | Ewers et al. | 423/308 |
| 4,959,104 A | 9/1990 | Iino et al. | 106/85 |
| 5,034,059 A | 7/1991 | Constantz | 106/161 |
| 5,037,639 A | 8/1991 | Tung | 424/57 |
| 5,047,031 A | 9/1991 | Constantz | 606/77 |
| 5,053,212 A | 10/1991 | Constantz et al. | 423/305 |
| 5,085,861 A | 2/1992 | Gerhart et al. | 424/78.17 |
| 5,129,905 A | 7/1992 | Constantz | 606/76 |
| 5,149,368 A | 9/1992 | Liu et al. | 424/602 |
| 5,152,836 A | 10/1992 | Hirano et al. | 424/423 |
| 5,164,187 A | 11/1992 | Constantz et al. | 424/423 |
| 5,178,845 A | 1/1993 | Constantz et al. | 423/305 |
| 5,262,166 A | 11/1993 | Liu et al. | 424/423 |
| 5,279,831 A | 1/1994 | Constantz et al. | 424/423 |
| 5,281,265 A | 1/1994 | Liu | 106/35 |
| 5,286,763 A | 2/1994 | Gerhart et al. | 514/772.4 |
| 5,336,264 A * | 8/1994 | Constanz et al. | 623/16 |
| 5,342,441 A | 8/1994 | Mandai et al. | 106/35 |

(List continued on next page.)

FOREIGN PATENT DOCUMENTS

| | | |
|---|---|---|
| EP | 0 268 463 | 5/1988 |
| EP | 0 347 028 | 4/1989 |
| EP | 0 664 133 | 7/1995 |
| JP | 63111875 | 5/1988 |
| JP | 63170205 | 7/1988 |
| JP | 2182261 | 7/1990 |
| JP | 5305134 | 11/1993 |
| JP | 06228011 | 8/1994 |
| JP | 7277712 | 10/1995 |
| WO | WO 92/02453 | 7/1991 |
| WO | WO 92/001009 | 1/1992 |
| WO | WO 94/04657 | 8/1993 |
| WO | WO 94/02412 | 2/1994 |
| WO | WO 94/20064 | 9/1994 |
| WO | WO 95/08319 | 9/1994 |
| WO | WO 96/36562 | 5/1996 |
| WO | WO 97/17285 | 11/1996 |

OTHER PUBLICATIONS

Norian Corporation, Product Information Sheet, "The Material Science of Norian SRS™, Skeletal Repair System™".

Rey et al., "Chemical Properties of Poorly Crystalline Apatites" *Phosphorus Res. Bull.* 6:67–70 (1996) abstract only.

Termine et al., "Amorphous/Crystalline Interrelationships in Bone Mineral" *Calc. Tiss. Res.* 1:8/23 (1967).

Yasue et al., "Effect of Adsorption of Succinic Acid on the Formation of Amorphous Calcium Phosphate" *Journal of the Ceramic Society of Japan* (Japanese Version) 102(12):1122–1127 (1994).

Aoki, "Science and medical applications of hyxroxyapatite," *JAAS*, pp. 11–15, 1991.

Appel et al., "Oncologic, Endocrine & Metabolic—Overview—Recent advances in implants for bone growth promotion", *Exp. Opin. Ther. Patents* 4(12):1461–1469, 1994.

Barton et al "Surface and bulk properties of amorphous calcium phosphate" *Colloid Interface Sci.* [Proc. Int. Conf.], 50th 3:71 (1976) [CA 87:73954v].

(List continued on next page.)

*Primary Examiner*—Shelley A. Dodson
(74) *Attorney, Agent, or Firm*—Hale and Dorr LLP

(57) ABSTRACT

The present invention provides delivery vehicles comprising a synthetic, poorly crystalline apatite (PCA) calcium phosphate and a biologically active agent. The PCA calcium phosphate offers many advantages over known delivery materials and is particularly useful for delivery of agents to bone sites, the central nervous system, intramuscular sites, subcutaneous sites, interperitoneal sites, and ocular sites. The invention also provides methods of preparing delivery vehicles, of altering delivery vehicle characteristics, and of delivering biologically active agents to a site. The invention is useful for both medical and veterinary applications.

57 Claims, 16 Drawing Sheets

U.S. PATENT DOCUMENTS

| | | | |
|---|---|---|---|
| 5,352,715 A | 10/1994 | Wallace et al. | 523/115 |
| 5,399,665 A | 3/1995 | Barrera et al. | 528/354 |
| 5,470,803 A | 11/1995 | Bonfield et al. | 501/1 |
| 5,496,399 A | 3/1996 | Ison et al. | 106/35 |
| 5,516,532 A | 5/1996 | Atala et al. | 424/548 |
| 5,522,893 A | 6/1996 | Chow et al. | 623/11 |
| 5,525,148 A | 6/1996 | Chow et al. | 106/35 |
| 5,542,973 A | 8/1996 | Chow et al. | 106/35 |
| 5,545,254 A | 8/1996 | Chow et al. | 106/35 |
| 5,565,502 A | 10/1996 | Glimcher et al. | 523/115 |
| 5,605,713 A | 2/1997 | Boltong | 427/2.1 |
| 5,665,120 A | 9/1997 | Ohtsuka et al. | 623/16 |
| 5,691,397 A | 11/1997 | Glimcher et al. | 523/115 |
| 5,700,289 A | 12/1997 | Breitbart et al. | 623/16 |
| 5,782,971 A | 7/1998 | Constanz et al. | 106/690 |

OTHER PUBLICATIONS

Benghuzzi et al., "Controlled release of hydrophilic compounds by resorbable and biodegradable ceramic drug delivery devices", *Biomed. Sci. Instrum.*, 28:179–182, 1992.

Benghuzzi et al., "Resorbable and biogradable ceramics as drug delivery systems", Abstract, Eighth Southern Biomedical Engineering Conference Richmond, VA, Oct. 15–16, 1989; *Biomater. Artif. Cells Artif. Organs*, 17:463, 1989.

Benghuzzi et al., "Alcap ceramic implantable devices and the effect of surface area on the delivery of various steroid hormones", Abstract, Eighth Southern Biomed. Engin. Conf., Richmond, VA, Oct. 15–16, 1989; *Biomater. Artif. Cells Artif. Organs*, 17:464, 1989.

Benghuzzi et al., "Long–term delivery of Danazol by biogradable ceramic devices", Abstract, Eighth Southern Biomedical Engineering Conference Richmond, VA, Oct. 15–16, 1989; *Biomater. Artif. Cells Artif. Organs*, 17:465, 1989.

Besic et al., "Electron probe microanalysis of noncarious enamel and dentin and calcified tissues in mottled teeth," *J. Dental. Res.*, 48:131, 1969.

Blumenthal et al. "Effect of preparation conditions on the properties and transformation of amorphous calcium phosphate," *Mat. Res. Bull.*, 7:1181–1189, 1972.

Boskey, Adele L., "Matrix Proteins and Mineralization: An Overview" *Connect. Tiss. Res.*, 357–363, 1996.

Cannon et al., "Continuous delivery of azidothymidine by hydroxyapatite or tricalcium phosphate ceramics", *Biomed. Sci. Instrm.*, 31:159–164, 1995.

Chung et al., "Biological effects of drug–loaded biodegradable membranes for guided bone regeneration" *J. Periodont. Res.*, 32:172–175. 1997.

Clarke et al., "Non–steriodal Anti–Inflammatory Drug Induced Differentiation of Bone Marrow Stromal Cells" 43rd Annual Meeting, *Ortho. Res. Soc.*, San Francisco, CA, 574, Feb. 9–13, 1997.

Constantz et al., "Skeletal Repair by in Situ Formation of the Mineral Phase of Bone," *Sci.*, 267:1976, 1995.

Dennissen et al., "New–shaped hydroxyapatite implants for release of agents modulating periodontal–like tissues" *J. Periodont. Res.*, 32:40–46, 1997.

Driessens et al., "Clacuim Phosphate Bone Cements" *Encycl. Hndbk. of Biomat. and Bioeng.*, NY Marcel Dekker, 855–877, 1995.

Ducheyne et al., "Bioceramic Composites", Chapter 15 from "An Introduction to Bioceramics, Advanced Series in Ceramics", vol. I.

Eanes et al. "Intermediate phases in the basic solution preparation of alkaline earth phosphates" *Calc. Tiss. Res.*, 2(1):38 (1968) [CA 69:110373f].

Eanes et al., "Intermediate states in the precipitation of hydroxapatite," *Nature*, 208:365–367, 1965.

Eanes, "Thermochemical Studies on Amorphous Calcium Phosphate," *Calc. Tiss. Res.*, 5:133, 1970.

Etex (Knaack et al) "Novel Fully Resorbable Calcium Phosphate Bone Substitute" 1997 *ASBMR Abst.*; 12(1):202, Aug., 1997.

Etex (D. Knaack) "Endothermically Setting Calcium Phosphate Bone Substitute" *Orthopaedic Congress*, Aug. 20–22, 1997, Boston MA.

Etex (Knaack et al) "A Fully Resorbable Calcium Phosphate Bone Substitute" *Portland Bone Symp.*, 1997.

Fabbri et al., "Hydroxyapatite–based porous aggregates: physico–chemical nature, structure, texture and architecture", *Biomaterials*, 16:225–228, 1995.

Glimcher et al., "Recent studies of bone mineral: Is the amorphous calcium phosphate theory valid?", *J. of Crystal Growth*, 53:100–119, 1981.

Glimcher, "Recent studies of the mineral phase in bone and its possible linkage to the organic matrix by protein–bound phosphate bonds," *Phil. Trans. Res. Soc. Lond.*, B 304:479–508, 1984.

Graves et al., "Resorbable ceramic implants", *J. Biomed. Mater. Res. Symp.*, No. 2(1):9–115, 1971.

Greenfield et al., "Formation chemistry of amorphous calcium phosphates prepared from carbonate containing solutions", *Calc. Tiss. Res.*, 9:152, 1972.

Hirasawa et al., "Manufacture of high purity hydroxyapatite", *Chem. Abst.*, 108(10):166, No. 78193h (Mar. 7, 1988).

Holmes et al., "Surface areas by gas adsorption on amorphous calcium phosphate and crystalline hydroxyapatite", *Calc. Tiss. Res.*, 7:163, 1971.

Hubbell, "Biomaterials in tissue engineering", *Bio/Techn.*, 13:56, 1995.

Ijntema et al., "Hydroxyapatite microcarriers for biocontrolled release of protein drugs", *Int'l J. of Pharm.*, 112:215, 1994.

Ikada et al., "Release of antibodic from composites of hydroxyapatite and poly(lactic acid)", *J. of Controlled Rel.*, 2:179–186, 1985.

Ishikawa et al. "Effects of preparation in aqueous solution on properties of hydroxyapatites" *Dent. Mater. J.* 9(1):58 (1990) [CA 113:218168j].

Itokazu et al., "Drug delivery systems using porous hydroxyapatite blocks", *J. Ortho. Surg.*, 2(2):47–50, 1994.

Jang, B.Z., "Advanced Polymer Composites", Chapter 1, Introduction, *The Mater. Info. Soc.*

Kim et al., "Effect of Recombinant Human (1–84) Parathyroid Hormone on Fracture Healing In Ovariectomized Rats" 43rd Annual Meeting, Orthopaedic Research Society, San Franscico, CA, 181–31, Feb. 9–13, 1997.

Labarthe et al., "Sur la structure et les propriétés des apatites carbonatées de type B phospho–calciques", *Ann. Chem.*, 8:289, 1973.

Mileti et al., "Development of a Hydroxyapatite ceramic matrix for the continuous delivery of coumadin", *Biomed. Sci. Instrum.*, 31:179–182, 1995.

Moldovan et al., "Continuous delivery of analgesics by ceramics", Abstract, *Fifth World Biomaterials Congress*, Toronto, Canada, Jun. 2, 1996.

Moldovan et al., "A ceramic system for continuous release of acetylsalicylic acid", *Biomed. Sci. Instrm.* 30:175–180, 1994.

Nolan et al., "Calcium hydroxyapatite ceramic delivery system", *J. Bone and Joint Surg.*, 75–13:334, 1993.

Nylen et al., "Molecular and ultrastructural studies of non–crystalline calcium phosphates", *Calc. Tiss. Res.*, 9:95, 1972.

Onodera et al., "Identification of Macrophage Migration Inhabitory Factor in Murine Neonatal Calvariae and Osteoblasts" 43rd Annual Meeting, Orthopaedic Research Society, San Francisco, CA, 322, Feb. 9–13, 1997.

Otsuka et al., "Effect of particle size of metastable calcium phosphates on mechanical strength of a novel self–setting bioactive calcium phosphate cement", *J. of Biomed. Mat. Res.*, 29:25–32, 1995.

Otsuka et al., "A novel skeletal drug delivery system using self–setting calcium phosphate cement. 9:Effects of the mixing solution volume on anticancer drug release from homogeneous drug–loaded cement", *J. of Pharm. Sci.*, 84(6), Jun. 1995.

Otsuka et al., "A novel skeletal drug–delivery system using self–setting calcium phosphate cement. 4. Effects of the mixing solution volume on the drug–release rate of heterogeneous aspirin–loaded cement", *J. of Pharm. Sci.*, 83(2), Feb., 1994.

Pool, "Coral chemistry leads to human bone repair", *Sci.*, 269:1772, Mar., 1995.

Posner et al., "Synthetic amorphous calcium phosphate and its relation to bone mineral structure", *Bone Min. Struct.*, 8:273–281, 1975.

Rey et al., "The carbonate environment in bone mineral: a resolution–enhanced fourier transform infrared spectroscopy study", *Calcif. Tissue Int.*, 45:157, 1989.

Rey et al., "Structural studies of the mineral phase of calcifying cartilage", *J. Bone Min. Res.*, 6:515, 1991.

Rey et al., "Preparation of Microporous Ceramic at Low Temperature from Poorly Crystalline Apatite" *Symposium Abstract*, 1993.

Shinto et al., "Calcium hydroxyapatite ceramic used as a delivery system for antibiotics", *J. of Bone and Joint Surg.*, 74B(4):600–604, Jul. 1992.

Shors et al., "porous hydroxyapatite" in An Introduction to Bioceramics (Hersch et al., eds), *Work Sci. Publ. Co. Pte. Ltd.*, 1993.

Thoma et al., "Biodegradable controlled release implants based on β–tricalcium phosphate ceramic", *Eur. J. Pharm. Biopharm.*, 38(3):107–112, 1992.

Thoma et al., "Biodegradable Gentamicin–Depotimplantate aus β– tricalcium–phosphatkeramik", *Pharmazie*, 46, 1991.

Tung et al., "An intermediate state in hydrolysis of amorphous calcium phosphate", *Calcif. Tissue Int.*, 35:783, 1983.

Tung et al., "In vitro drug release of antibiotic–loaded porous hydroxyapatite cement", *Art. Cell, Blood Subs., and Immob. Biotech.*, 23(1):81–88, 1995.

Uchida et al., "Slow release of anticancer drugs from porous calcium hydroxyapatite ceramic", J. *of Ortho. Res.*, 10:440–445, 1992.

* cited by examiner

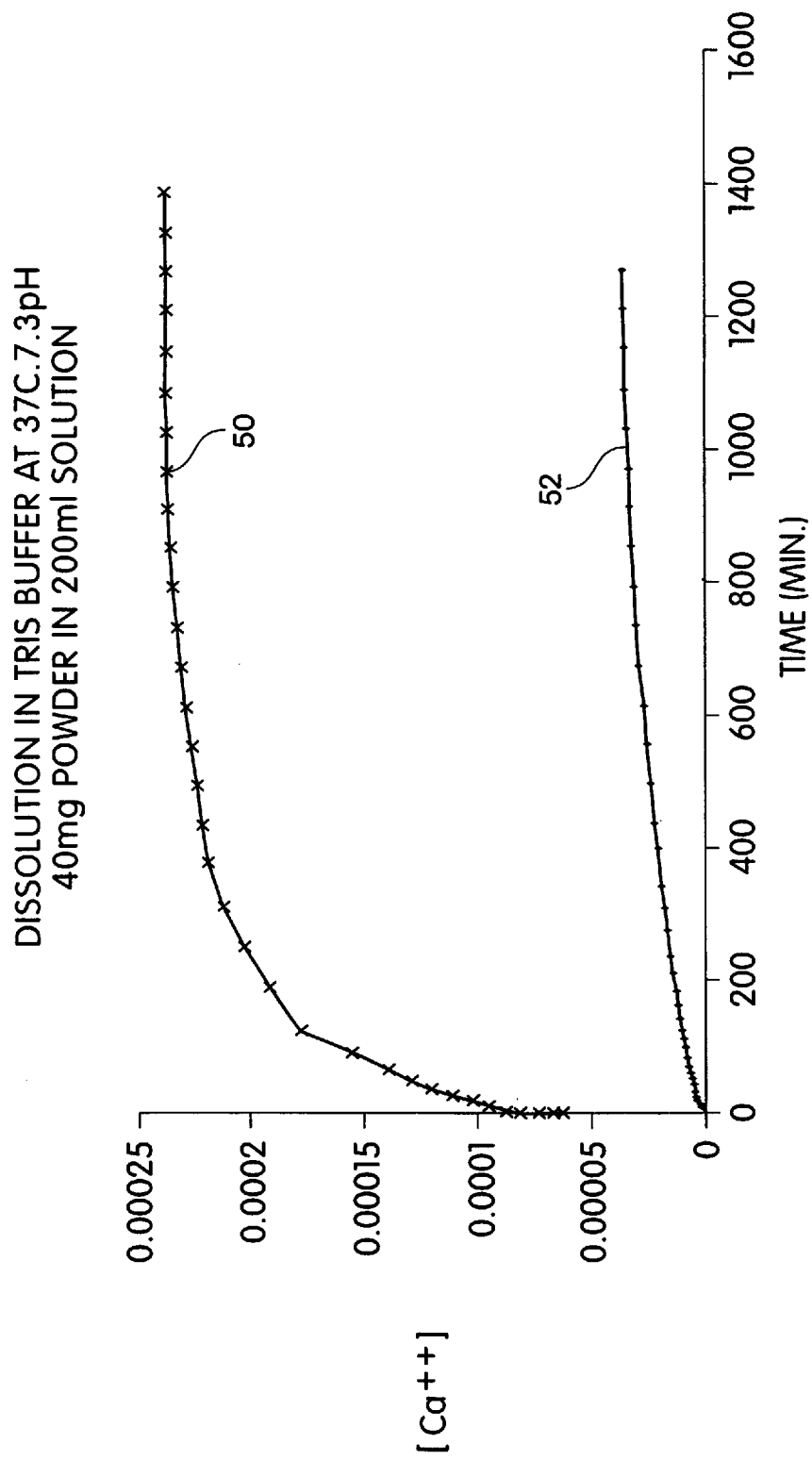

DELIVERY VEHICLE

This application is a continuation-in-part application of co-pending application U.S. Ser. No. 08/650,764 filed May 20, 1996 entitled "Novel Bone Substitution Material and a Method of Its Manufacture" now U.S. Pat. No. 6,214,368, which is a continuation-in-part application of co-pending application U.S. Ser. No. 08/446,182 filed May 19, 1995 entitled "Synthesis of Reactive Amorphous Calcium Phosphates" now U.S. Pat. No. 5,676,976, each of which is incorporated herein by reference. This application is also related to commonly-owned applications entitled "Cell Seeding of Ceramic Composites" U.S. Ser. No. 08/729,354,; "Conversion of Amorphous Calcium Phosphate to Form a Novel Bioceramic", U.S. Ser. No. 08/729,344; "Orthopedic and Dental Ceramic Implants" U.S. Ser. No. 08/729,343; and "Bioactive Ceramic Composites" U.S. Ser. No. 08/722,016, each of which is filed on even date herewith and is incorporated herein by reference.

BACKGROUND OF THE INVENTION

Much research in the area of biopharmaceutics is directed toward the development of effective implantable drug delivery vehicles. Such vehicles must be biocompatible and also must be capable of protecting the activity of the biologically active agent they are intended to deliver. Many biologically active agents are labile and easily lose activity when they are incorporated into a delivery material. Preservation of protein activity has posed particularly difficult problems.

Calcium phosphate ceramics have been studied as potential drug delivery systems due to their well known biocompatibility and their affinity for protein reagents (see, for example, IJntema et al., *Int. J. Pharm.* 112:215, 1994; Itokazu et al., *J. Orth. Surg.* 2:47, 1994; Shinto et al., *J. Bone Joint Surg.* 74-B:600, 1992; Uchida et al., *J. Orth. Res.* 10:440, 1992). However, the reactions employed to produce known calcium phosphate ceramic materials typically require elevated temperatures and/or pressures, and also require the presence of acids or bases. Because most biologically active agents would be destroyed by one or more of the conditions required to produce the ceramic, the biologically active agents can only be loaded in after the material is produced, which can limit the amount and type of agent that can be delivered.

Also, although a number of calcium phosphate materials have been referred to as "resorbable", such compounds, usually comprising or derived from tricalcium phosphate, tetracalcium phosphate or hydroxyapatite are in fact only weakly resorbable. Of the group, the tricalcium phosphate compounds have been demonstrated to be the most resorbable and, after many years of study, they are still not widely used in clinical settings. The tricalcium phosphates are known to have lengthy and somewhat unpredictable resorption profiles, generally requiring in excess of one year for resorption. Unless steps are taken to produce extremely porous or channeled tricalcium phosphates, these compounds are not replaced by bone. Recent studies have lead to the conclusion that the "biodegradation of TCP, which is higher than that of [hydroxyapatite], is not sufficient" (Berger et al., *Biomaterials*, 16:1241, 1995).

Tetracalcium phosphate and hydroxyapatite derived compounds are also only weakly resorbable. Published reports of tetracalcium phosphate fillers generally describe partial resorption over long periods of time. For example, as reported by Horioglu et al., it is not uncommon for such materials to require 30 months for 80% resorption (*Soc. for Biomatenals*, pg. 198, Mar. 18–22, 1995). Also, many reports that describe "resorption" of calcium phosphate materials do not actually demonstrate resorption because the authors do not rule out, for example, migration of the vehicle from the implant site (see, for example, IJntema et al., supra).

There remains a need for the development of a drug delivery vehicle that is biocompatible, fully resorbable, and not detrimental to drug activity. Preferably, the resorption rate of the material should be modifiable in known ways. Also, the material should be easy to manufacture, preferably using mild reaction conditions.

DEFINITIONS

"Amorphous"—By "amorphous" as that term is used here, it is meant a material with significant amorphous character. Significant amorphous character contemplates greater than 75% amorphous content, preferably greater than 90% amorphous content, and is characterized by a broad, featureless X-ray diffraction pattern. It is recognized that a small degree of crystallinity may exist in the material. However, for the amorphous precursor materials of the present invention, it is preferable that the degree of crystallinity be less than that desired in the product material.

"Bioactive"—"Bioactive" refers to a material that induces hard tissue formation in and about the implant. When implanted in soft tissue, the bioactivity may also require the presence of a growth or trophic factor, or the seeding of the implant with a hard tissue forming cell type.

"Biocompatible"—The term "biocompatible", as used herein, means that the material does not elicit a substantial detrimental response in the host. There is always concern, when a foreign object is introduced into a living body, that the object will induce an immune reaction, such as an inflammatory response that will have negative effects on the host. For example, although hydroxyapatite is generally considered to be "biocompatible", significant inflammation and tissue necrosis have been observed when crystalline hydroxyapatite microcarriers are inserted intramuscularly in animals (see, for example, IJntema et al., *Int. J. Pharm* 112:215 (1994)).

"Bioresorbable"—"Bioresorbable" refers to the ability of a material to be resorbed in vivo. "Full" resorption means that no significant extracellular fragments remain. The resorption process involves elimination of the original implant materials through the action of body fluids, enzymes or cells. Resorbed calcium phosphate may, for example, be redeposited as bone mineral, or by being otherwise reutilized within the body, or excreted. "Strongly bioresorbable", as that term is used herein, means that at least 80% of the total mass of material implanted intramuscularly or subcutaneously is resorbed within one year. In preferred embodiments of the invention, the strongly resorbing PCA calcium phosphate is characterized in that, when at least 1 g (preferably 1–5 g) of PCA material is implanted at a subcutaneous or intramuscular site, at least 80% of the material is resorbed within one year. In more preferred embodiments, the material will be resorbed within nine months, six months, three months, and ideally one month. Furthermore, particularly preferred materials are characterized in that they can be fully resorbed in the stated time periods. For the purpose of this disclosure, "weakly" resorbable means that less than 80% of the starting material is resorbed after one year.

"Effective Amount"—An effective amount of a biologically active agent is an amount sufficient to elicit a desired biological response.

"Hardening"—"Hardening" refers to the process by which the hydrated precursor is transformed into a hardened PCA material. The PCA material is considered to be "hardened" when it is a substantially non-formable solid. Such a hardened PCA material has minimal compressibility and tends to undergo plastic as opposed to elastic deformation.

"Hydrated precursor"—The term "hydrated precursor", as used herein, refers to the paste or putty formed by hydration of the dry PCA precursors in the presence of a limited amount of aqueous solution (i.e., less than approximately 1 mL aqueous solution/1 g precursor powder). The hydrated precursor may comprise both reactants and products, in various combinations, depending on the extent to which the conversion has progressed. Both the "injectable" and "formable" PCA precursor pastes described herein are hydrated precursors. Preferred "injectable" hydrated precursors have a consistency appropriate for delivery through an 18 gauge needle.

"Poorly crystalline apatitic calcium phosphate", "PCA calcium phosphate" and "PCA material", as those terms are used herein, describe a synthetic poorly crystalline apatitic calcium phosphate. The PCA material is not necessarily restricted to a single calcium phosphate phase provided it has the characteristic XRD and FTIR pattern. A PCA calcium phosphate has substantially the same X-ray diffraction spectrum as bone. The spectrum is generally characterized by only two broad peaks in the region of 20–35° with one centered at 26° and the other centered at 32°. An additional broad shoulder occurs at approximately $2\theta=29$ and another may be present at approximately $2\theta=33.6$. Absent from the spectra are any additional sharp peaks or sharp shoulders characteristic of crystalline hydroxyapatite occurring in the range of $2\theta=27-34$. In particular, there are no sharp peaks or shoulders corresponding to Miller's Indices for 210, 112, or 300 for hydroxyapatite. It is further characterized by FTIR peaks at 563 $cm^{-1}$, 1034 $cm^{-1}$, 1638 $cm^{-1}$ and 3432 $cm^{-1}$ ($\pm 2$ $cm^{-1}$). Sharp shoulders are observed at 603 $cm^{-1}$ and 875 $cm^{-1}$, with a doublet having maxima at 1422 $cm^{-1}$ and 1457 $cm^{-1}$.

"Promoter" —The term "promoter", as used herein, describes a material or treatment that promotes hardening of a hydrated precursor and may enhance the ACP to PCA calcium phosphate conversion. Some promoters participate in the conversion and are incorporated into the product PCA material; others, known as "passive" promoters, do not participate.

"Reactive"—"Reactive" is used herein to refer to the ability of an amorphous calcium phosphate when mixed with liquid to form a hydrated precursor to undergo conversion to the PCA material of the present invention in the presence of a promoter in association with hardening of the precursor materials. Preferred ACPs are characterized by an ability to convert completely, an ability to convert quickly with hardening, an ability to undergo conversion with otherwise inert compounds and/or an ability to convert into a substantially homogeneous PCA material. Where the ACP is reacted with a second calcium phosphate, the "conversion" can encompass conversion of both the ACP and the second calcium phosphate. The degree of hardening and the kinetics of the hardening process are also important elements of reactivity. Some ACPs are more reactive than others. An ACP is considered "highly reactive" if it undergoes conversion and hardening to a PCA material in the presence of a weak promoter, such as dicalcium phosphate dihydrate ("DCPD") with a grain distribution containing a significant fraction of grain sizes greater than 100 $\mu$m. Preferred highly reactive ACPs produce a hardened PCA material in the presence of weakly promoting DCPD and water at 37° C. in less than twelve hours, with hardening being substantially complete in about one to five hours, and ideally 10–30 minutes.

SUMMARY OF THE INVENTION

The present invention provides a delivery vehicle for biologically active agents that has excellent biocompatibility and is bioresorbable. The delivery vehicle is comprised of a synthetic, poorly crystalline apatitic (PCA) calcium phosphate material. The PCA material of the present invention is strongly bioresorbable. That is, when an implant comprising at least 1 g of material is implanted in pellet form in an intramuscular or subcutaneous site, at least approximately 80% of the material is resorbed within one year, preferably within 9 months, 6 months, 3 months, and, ideally 1 month. More preferably, at least 80% of a 5 g implant is resorbed within these time frames. It will be appreciated that the conformation of the material (e.g., in a sphere as compared with a rod or other shape) may affect is resorption rate. Furthermore, the resorption rate of the delivery vehicle can be varied through its manner of preparation.

The synthetic PCA material utilized in the delivery vehicle of the present invention is compatible with a wide array of biologically active agents and can be employed to deliver agents to any of a variety of sites in the body. The material is characterized by a distinctive X-ray diffraction pattern that reveals its poor crystallinity. Preferably, the material has a calcium to phosphate ratio in the range of about 1.1 to 1.9. More preferably, this ratio is in the range of about 1.3 to 1.5.

In preferred embodiments of the present invention, the synthetic PCA material is formed in a reaction in which at least one amorphous calcium phosphate (ACP) precursor is exposed to a promoter. In particularly preferred embodiments, the promoter comprises a second calcium phosphate material. The reaction conditions employed to produce the PCA material utilized in the present invention are mild, so that biological agents can be incorporated into the material during the formation reaction, if desired. Alternatively, the agents may be incorporated after the delivery vehicle is made. The delivery vehicle material may be formed into any of a variety of useful delivery shapes, either before or after the introduction of biologically active agent, and may be delivered to the site by, for example, injection or surgical implantation. The material may be introduced into a site in a wet, non-hardened state (i.e., as a hydrated precursor) and allowed to harden in situ. The vehicle may alternately be hardened in wiro at an elevated temperature, generally at or above 37° C., and thereafter surgically implanted into a subject (animal or human). The device may be fabricated in vitro either in the presence or absence of the therapeutic agent. The therapeutic agent may be added post-hardening by exposing the pre-formed vehicle to the agent. One advantage of the delivery system of the present invention is that it allows a high local concentration of drug to be achieved, which is particularly useful with drugs that have toxic side effects and also with labile drugs.

The present invention therefore provides vehicles for delivering biologically active agents, which vehicles comprise a PCA calcium phosphate and a biologically active agent. The inventive vehicles optionally comprise, for example, other bioresorbable materials, erosion rate modifiers, cells, or other factors that modify one or more characteristics of the vehicle (such as its strength, adherence, injectability, frictional characteristics, etc.).

The invention also provides methods of preparing delivery vehicles, of altering delivery vehicle characteristics, and of delivering biologically active agents to a site. Preferred delivery sites include both in vitro and in vivo sites. The delivery vehicles of the invention are suitable for delivery into human or animal sites. Preferred in vivo sites include bony sites, intramuscular sites, interperitoneal sites, subcutaneous sites, central nervous system sites, and occular sites.

DESCRIPTION OF THE DRAWINGS

FIG. 3 is a solubility curve of a poorly crystalline apatitic calcium phosphate product derived from amorphous calcium phosphate of the present invention, as compared with a crystalline hydroxyapatite. Note the relative higher solubility of the material of the present invention versus a more crystalline form of hydroxyapatite, as measured by the amount of calcium ions released into solution at 37° C.;

FIG. 10 presents photomicrographs of tibial defects either untreated (10a) or treated (10b) with a delivery vehicle of the present invention.

DESCRIPTION OF PREFERRED EMBODIMENTS

Preparation of Delivery Vehicle

Figure 1:
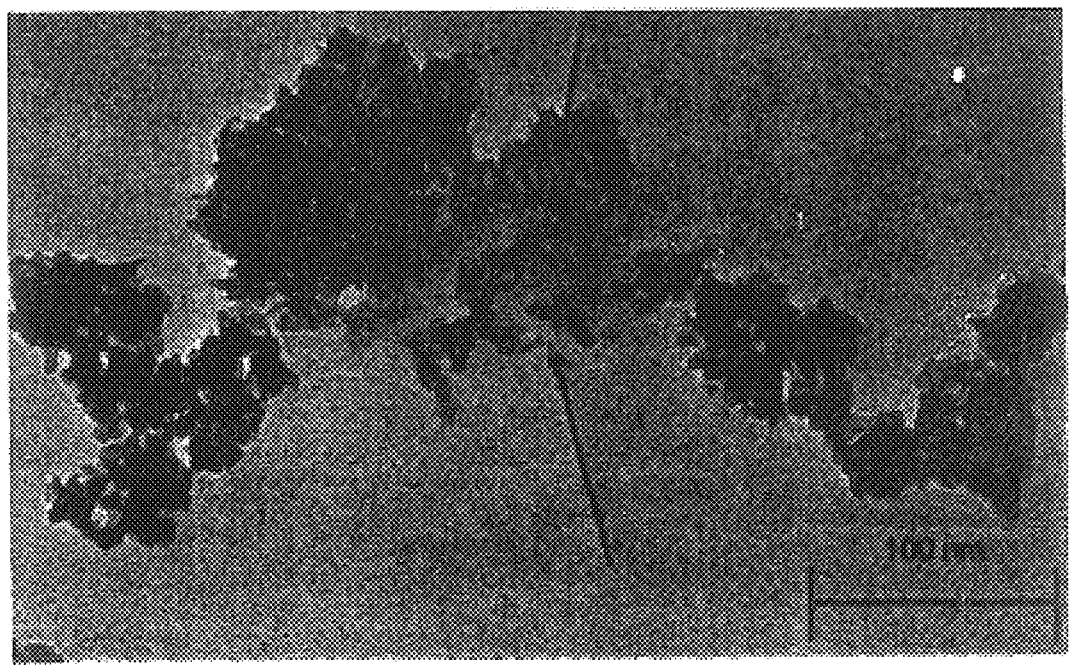
FIG. 1 is a high-resolution transmission electron micrograph of the reactive amorphous calcium phosphate illustrating the nanometer-sized grains in clusters with relatively unclear boundaries and partially immersed in shapeless form (arrows)

The delivery vehicle of the present invention is a synthetic, poorly crystalline apatitic calcium phosphate material. In preferred embodiments, it is the material described in co-pending applications U.S. Ser. No. 08/650,764 and/or U.S. Ser. No. 08/446,182, each of which is incorporated herein by reference.

The PCA material employed in the present invention is characterized by its biocompatibility, its biological resorbability and its minimal crystallinity. The material may be highly porous and rapidly resorbable or of decreased porosity and slowly resorbable. Its crystalline character is substantially the same as natural bone, and lacks the higher degree of crystallinity seen in the bone substitute materials known to the art. The inventive PCA material also is biocompatible and not detrimental to the host.

The delivery vehicles of the present invention may be implanted in a patient in a paste or putty form (i.e., as a hydrated precursor). Since the inventive reaction that produces the hardened PCA material can be initiated outside the body, and proceeds slowly at room temperature, the possibility that the material will "set up" prior to application to the surgical site and become unusable is minimized. The reaction accelerates significantly at body temperature and the material hardens in place. This feature is particularly useful in the surgical setting, where custom fitting of the device to the implant location is typically required. For example, in some preferred embodiments of the invention, an antibiotic and/or regenerative factor is delivered to a fracture site. In such embodiments, the inventive paste containing the therapeutic agent will be applied to and used to fill a fracture site, as well as to deliver the desired agent.

Alternatively, the inventive delivery vehicles may be pre-hardened outside the body, loaded with the desired biological agent, and implanted at a later time. This approach is useful in those situations where custom shapes are not essential, and where production of large numbers of vehicles is desired.

Generally, the formation reaction of the present invention is completed after application to the surgical site. The material typically hardens in less than five hours, and substantially hardens in about one to five hours, under physiological conditions. Preferably, the material is substantially hardened within about 10–30 minutes. The consistency and formability of the PCA material, as well as the speed of the formation reaction, may be varied according to the therapeutic need by modifying a few simple parameters.

The resorbability of the PCA material employed in the instant invention is attributable to the combination of its porosity, its chemical composition, and its crystallinity. Apatites have reduced crystalline characters and display somewhat increased solubility in aqueous systems when compared with more crystalline species. The low crystallinity of the inventive PCA material, and/or the presence of stable amorphous domains within it, is believed to promote its resorbability in biological systems.

The resorbability of the PCA material of the present invention can be modified by altering its density and/or porosity. Porosity facilitates both the diffusion of substances to and from the interior of the material and, in certain applications, the penetration of cells and cell processes into the material matrix. Drug delivery materials of lower porosity tend to resorb more slowly in vivo than do those of higher porosity. In one embodiment of the invention, porosity is increased through the use of a dry mixture of controlled particle size reactants; in other embodiments, chemical or physical etching and leaching techniques are Thus, different embodiments of the present invention provide PCA materials with different resorption rates. Selection of reactants, porosity, final crystallinity, and amounts and types of crystallization inhibitors employed yields different embodiments of the PCA material of the present invention, so that, in different embodiments, 1 g of material is resorbed (i.e., at least 80% resorbed) within any desired time period from 2 weeks to 1, 3, 6, or 9 months, to 1 year.

In a preferred embodiment of the present invention, the reaction that produces the PCA material is initiated by adding physiological saline to a mixture of two dry components so that a thick paste forms that hardens in about a half an hour. Other aqueous agents, such as serum, tissue culture medium, or another buffered solution, or distilled water, may be used in place of saline. Most often, the resulting resorbable PCA material will be "calcium deficient", with a calcium to phosphate ratio of less than 1.5 as compared to the ideal stoichiometric value of approximately 1.67 for hydroxyapatite.

The invention provides a test for identifying suitable PCA materials and reactive precursors. Specifically, precursors are combined, are hydrated with a limited amount of water (so that a paste or putty is formed), and are allowed to harden into a PCA material. Desirable precursors are capable of hardening in a moist environment, at or around body temperature. The hardened product is then placed intramuscularly or subcutaneously in a test animal. Desirable materials are those that, when implanted as an at least 1 g pellet are at least 80% resorbed within 1 year (or less). Preferably, the material can be fully resorbed. Generally, it is easier to test resorption of gram quantities of material in subcutaneous sites.

The PCA material of the present invention is formed in a reaction that employs at least one amorphous calcium phosphate (ACP) precursor, preferably an activated ACP (see, for example, Examples 1–4). In some instances, the reaction may employ only one precursor ACP, which is converted in a controlled fashion in part or whole to the PCA material of the invention. Alternatively, the reaction may employ a promoter that comprises one or more additional precursors (preferably one or more calcium and/or a phosphate sources), that combine with the ACP to yield the PCA material of the invention. Also, a non-participating promoter may be employed to facilitate conversion of the activated ACP to the inventive PCA material. In any event, reactions that can be initiated outside of the body, that can be carried on in a paste-like configuration, and that significantly accelerate at 37° C. leading to a hardened calcium phosphate product are greatly preferred.

The conversion of ACP to a PCA material is promoted in the presence of water. Generally, the ACP is provided as a powder is combined with any other reactants (e.g. a second calcium phosphate), and is exposed to a limited amount of water, so that a paste or putty is formed. The hydrated precursor then hardens, and the hardening is associated with formation of the PCA material. It is an aim of this invention to provide methods which promote the conversion of ACP to a PCA material in a controlled fashion, producing a hydrated precursor paste or putty that hardens predictably and has utility in dental, orthopedic, drug delivery, cell therapy, and/or other therapeutic applications. The promoters used to accomplish this conversion may themselves be converted to PCA material, or may participate in other chemical or physical reactions. Some preferred promoters may also remain unchanged during the conversion, providing a catalytic or nucleator function. Particularly suitable in this regard are substances that provide reactive surfaces that weakly promote crystallization to produce PCA calcium phosphate.

ACP precursors only: When amorphous calcium phosphate is used as the sole precursor to produce a resorbable delivery vehicle, it is important to control the natural tendency of the ACP to convert to highly crystalline hydroxyapatite. On the other hand, the time course of conversion should be fast enough to have surgical utility. One approach is to combine a precursor ACP containing an inhibitor of crystal formation (e.g., the ACP of Example 1) with an ACP that does not contain an inhibitor of crystal formation (e.g., a promoter). The reactants may be mixed in a dry state, with the appropriate particulate size and an excess of the inhibitor-containing ACP. The reactants can then be exposed to crystal-forming conditions such as the addition of water, followed by an elevation in temperature (e.g., as occurs following introduction into the body), to convert the reactants to the PCA material of the invention. Other methods of controlled conversion involve the use of catalysts.

ACP precursor plus additional calcium phosphate sources: ACP may be reacted with a second calcium source (including a second ACP) using any reaction-promoting technique. In preferred embodiments, the second calcium source is itself a promoter. The reaction being promoted is the conversion of an amorphous calcium phosphate into a hardened water nanocrystalline or poorly crystalline apatitic calcium phosphate. Such reactions include acid/base, displacement, substitution, and hydrolysis reactions as well as purely physical and mechanical reactions (e.g., grinding, mixing). Catalytic conversion, such as surface-catalyzed conversion of ACP to a PCA material, may also be employed. Under any reaction scheme, it is important that the ACP retains significant amorphous character throughout the reaction. Specifically, the overall crystallinity within the starting ACP should not exceed that desired in the end product. Thus, certain reaction schemes may require stabilization of the amorphous nature of the ACP throughout the reaction period. Examples inhibitors of crystal formation that are known to the art and are useful for such stabilization include carbonate, pyrophosphate and magnesium.

In some preferred embodiments, the ACP component is activated under heat in order to facilitate the conversion being promoted by the second calcium containing reactant or other promoter. Examples of suitable such second reactant promoters include DCPD, other crystalline or poorly crystalline calcium phosphates, calcium sources, phosphate sources, or a second ACP. Other methods of promoting conversion, such as catalysis or the use of ionic solvents or promoters of nucleation, may also be employed to promote reaction between substituents. The second calcium phosphate reactant may be of any crystalline structure and should be chosen so as to be reactive with the first ACP either directly or through the use of reaction enhancing vehicles such as ionic solvents or catalysts. Appropriate reaction conditions will be determined by demonstration of rapid hardening at 37° C. after the reactants are mixed and water is added.

The delivery vehicle formation reaction may also be designed to produce an end product that is porous. In one embodiment, the use of a dry mixture of controlled particle size reactants, leads to a porous material. Other methods of promoting porosity, such as chemical or physical etching and leaching, may be employed.

The present invention provides a novel process for activating a standard amorphous calcium phosphate precipitate into highly reactive amorphous solids. The amorphous solids can be used in the reactions described above to form a poorly- or nanocrystalline synthetic apatitic calcium phosphate that provides bioactivity, bioresorbability and structural integrity. The novel amorphous material can be reacted with other calcium phosphates at or below 37° C. to form a bone-like material consisting of poorly crystalline apatitic calcium phosphate.

Prior art acid-base reactions of conventional crystalline calcium phosphates produce poorly reacted solids, having reaction products that are too crystalline to be sufficiently resorbable in living tissues. The reactions from the prior art are generally incomplete and the reaction products are inhomogeneous. In contrast, the amorphous calcium phosphate of the present invention reacts quickly and completely with a wide variety of calcium phosphates and other calcium- or phosphorus-bearing materials to provide a homogeneous product.

The source of the enhanced reactivity of the ACP of the present invention is not completely understood; however, it is believed to be associated with the amorphicity (lack of crystallinity) and, in some embodiments, ion pair site vacancies in the material, as created by the process of the present invention. The vacancies may provide reactive sites for subsequent reaction. These observations will be discussed more fully, below.

The method of the present invention permits initial formation of amorphous calcium phosphate particles of less than 1000 Å, preferably 200–500 Å, and most preferably 300 Å, the further growth of which is curtailed by rapid precipitation of the product from solution. During reaction of calcium and phosphate ion sources to form an amorphous calcium phosphate, a third ion is introduced in the solution so that this third ion is incorporated in the amorphous precipitate structure instead of trivalent $PO_4^{3-}$ group(s). Because some $PO_4^{3-}$ is replaced by the third ion, the overall $PO_4^{3-}$ decreases, thus increasing the Ca/P ratio of the amorphous precipitate (as compared to standard amorphous calcium phosphate) and modifying the valence or charge state of the calcium phosphate. The amorphous solids then may be rapidly freeze-dried to preserve the chemical and physical properties of the material. The amorphous solids then may be treated under specific conditions selected to promote removal of at least some of the third ion. Where the third ion is carbonate, specific temperature and pressure conditions lead to the reduction of total carbon, presumably as gaseous carbon dioxide from the amorphous solid, while maintaining the product amorphicity.

The resultant material is an amorphous solid with a higher Ca/P ratio than is typically found in amorphous calcium phosphates, where the ratio generally reported in the past is 1.50. Further, removing carbon from the material results in a vacancies in the interstitial structure within the amorphous solids, rendering it a highly reactive solid. There may be several possible vacancies sources. The material possesses a porosity which promotes reactivity by various means, such as increased surface area. The material may also undergo a change in the stoichiometry balance upon removal of the third ion. This stoichiometry change may result a charge imbalance which is responsible for the increased reactivity of the amorphous calcium phosphate.

It is desirable to maintain substantial amorphous character within the material throughout the entire process. If crystallinity in its entirety (single crystalline regions), or even in local domains (microcrystalline regions), is introduced to excess during the process or in the final product, the solid has been found to be less reactive. The resultant highly reactive calcium phosphate is amorphous in nature and has a calcium to phosphorous ratio in the range of 1.55 to 1.65. In a preferred embodiment, the amorphous calcium phosphate has a Ca/P ratio of about 1.58.

The amorphous state of the amorphous calcium phosphate is induced by controlling the rate and duration of the precipitation process. The amorphous calcium phosphate of the present invention is precipitated from solution under conditions where initial precipitation is rapid. Rapid precipitation results in the formation of many extremely small calcium phosphate nuclei. Additionally, rapid crystal or grain growth leads to the production of more defects within each grain, thereby also increasing solubility. At the extreme end of the spectrum, crystal or grain growth is so rapid and defect density is so significant that an amorphous calcium phosphate results. Amorphous calcium phosphate is gel-like and includes solid solutions with variable compositions. These gels have no long range structure, but are homogeneous when measured on an Angstrom scale. Under physiological conditions, these amorphous compounds have high solubilities, high formation rates and high rates of conversion to poorly crystalline apatitic calcium phosphate.

The amorphous calcium phosphate solids acquired by this method retain their amorphous nature sufficiently long enough to be introduced into the final reaction as substantially amorphous solids. They can also be mixed and reacted with other solids or solutions containing phosphates, to obtain solids containing a homogeneous distribution of nanometer-sized crystals. Further, in preferred embodiments, because the amorphous calcium phosphate reacts completely with the other solids, the Ca/P of the resultant solid will constitute the total calcium and phosphorous from such reaction, i.e., there will be an essentially complete reaction. When a proper molar concentration of phosphate from the solution or solids is reacted with the novel amorphous calcium phosphate material, a poorly crystalline apatitic calcium phosphate material (Ca/P 1.1–1.9) is obtained. Thus, the present invention permits one to design and modify the chemical composition of the resultant product, thereby providing a further mode of controlling bioactivity of the final product used as a delivery vehicle.

In one embodiment of the present invention, a solution is prepared that contains calcium and phosphate ions and a third ion in a concentration, at a pH, and at a temperature that will promote the rapid nucleation and precipitation of calcium phosphate. When precipitation is sufficiently rapid, an amorphous gel-like calcium phosphate is formed. Because the thermodynamically favored crystalline form of hydroxyapatite is enhanced by reducing the rate of reaction, certain processing steps of increasing the rate of reaction may be taken to ensure that an amorphous compound is obtained. The following factors, among others, are to be considered when designing a solution for the rapid precipitation of the amorphous calcium phosphate of the present invention.

Preferred conditions: Rapid mixture of calcium and phosphate sources to increase the rate of reaction. The rate of reaction is increased to favor non-stable phases as a product. Allowing more reaction time for each of the ions to juxtapose correctly to form a solid will result in a more thermodynamically favorable crystalline and stable structure.

Preferred calcium and phosphate sources: The use of highly concentrated or near supersaturation solutions ensures that a more rapid reaction will occur.

Preferred temperature: Although the reaction can be carried out at room temperature, temperatures of near boiling point to increase the concentration of one reactant is a possible means of increasing the rate of reaction.

In one embodiment calcium ions, phosphate ions and carbonate ions are mixed together rapidly in an aqueous solution to obtain a carbonate containing amorphous calcium phosphate solid. The relative concentrations of the ions are selected to give a precipitate having the desired Ca/P ratio. The carbonate ion substitutes for a phosphate ion in the amorphous calcium phosphate. The carbonated amorphous calcium phosphate may be obtained by precipitation from an aqueous carbonate solution. Suitable aqueous carbonate solutions include, by way of example only, bicarbonate solution, sodium carbonate solution, potassium carbonate solution. It is further contemplated as within the scope of the invention to use non-aqueous solutions.

Use of a carbonated material is desirable because it permits manipulation of the Ca/P ratio by substitution of $PO_4^{3-}$ by $CO_3^{2-}$. Additionally, the presence of $CO_3^{2-}$ is known to retard the development of crystallinity in amorphous calcium phosphate. Is recognized, however, that other ions or a mixture of ions may be suitable in place of or in addition to carbonate ion in modifying the Ca/P ratio and in introduction of reactive site vacancies into the amorphous calcium phosphate, such as by way of example only, nitrate, nitrite, acetate, $Mg^{+2}$ and $P_2O_7^{4-}$ ions.

The amorphous calcium phosphate precipitate may be collected and filtered prior to activation. It is preferred to perform this step in a cold room or at sub-ambient temperatures so as to preserve the amorphous state of the precipitate collected. Collection may typically be carried out by any conventional means, including, but in no way limited to, gravity filtration, vacuum filtration or centrigation. The collected precipitate is gelatinous and is washed more than once with distilled water.

The washed precipitate is then dried under any conditions that maintain the amorphous character of the material. Lyophilization is a suitable, but not exclusive, technique. The precipitate is frozen and, while being kept frozen, is dried to remove the bulk of the entrained liquid. This procedure may be accomplished by placing the frozen precipitate into a vacuum chamber for a given period of time. Freeze-drying typically occurs at liquid nitrogen temperatures for a time in the range of 12–78 hrs, preferably about 24 hours, and under a vacuum in the range of $10^{-1}$–$10^{-4}$, preferably $10^{-2}$, torr. A preferred method includes lyophilization because the cryogenic temperatures typically used in lyophiization inhibit further crystallization of the material. As a result, the amorphous calcium phosphate obtained thereby is an extremely fine free flowing powder.

The dried ACP may then be activated. In a preferred embodiment, where carbonate is present in the ACP, the ACP powder is heated to drive off remaining free water and water of hydration and to remove carbon, presumably through the decomposition of $CO_3^{2-}$ into $CO_2$ and oxygen. The heating step is carried out at a temperature of less than 500–600° C. but more than 425° C., so as to prevent conversion of the amorphous calcium phosphate into crystalline hydroxyapatite. Heating is preferably carried out at a temperature in the range of 450–460° C., preferably for ½ hour to 6 hours.

Low crystallinity and site vacancies (porosity and/or stoichiometric changes) may account for the observed higher reactivity of the activated amorphous calcium phosphate of the present invention. This is exemplified by the following observations. A carbonate-containing amorphous calcium phosphate which has been heated to 525° C. is observed to have an increase in formation of crystalline hydroxyapatite and to have a corresponding decrease in reactivity. Amorphous calcium phosphate that is heated to only 400° C. retains its amorphous characteristic, but exhibits a decreased reactivity. Presumably this decrease in reactivity is related to the higher carbonate levels (and fewer site vacancies) observed by IR in samples treated at this lower temperature. These findings suggest that both amorphicity and decreased carbon content (vacant reactive sites) are a factor in reactivity. This is not intended to be in any way an exclusive basis for reactivity. Other basis for the observed reactivity are considered to be within the scope of the invention. The resulting amorphous calcium phosphate powder is a highly reactive amorphous calcium phosphate material with a Ca/P ratio of between 1.1–1.9, preferably about 1.55 to 1.65, and most preferably about 1.58. The powder has been characterized by a variety of analytical techniques.

In FIG. 1, a high-resolution transmission electron micrograph is shown to illustrate the morphological characteristics and the angstrom-sized nature of the preferred reactive amorphous calcium phosphate of the present invention. Preferred particle sizes are less than 1,000 Å, preferably in the range of 300–400 Å. Note the unclear boundaries separating the globule-like clusters, lacking clear edges and surfaces, in contrast to crystalline materials.

Figure 2:
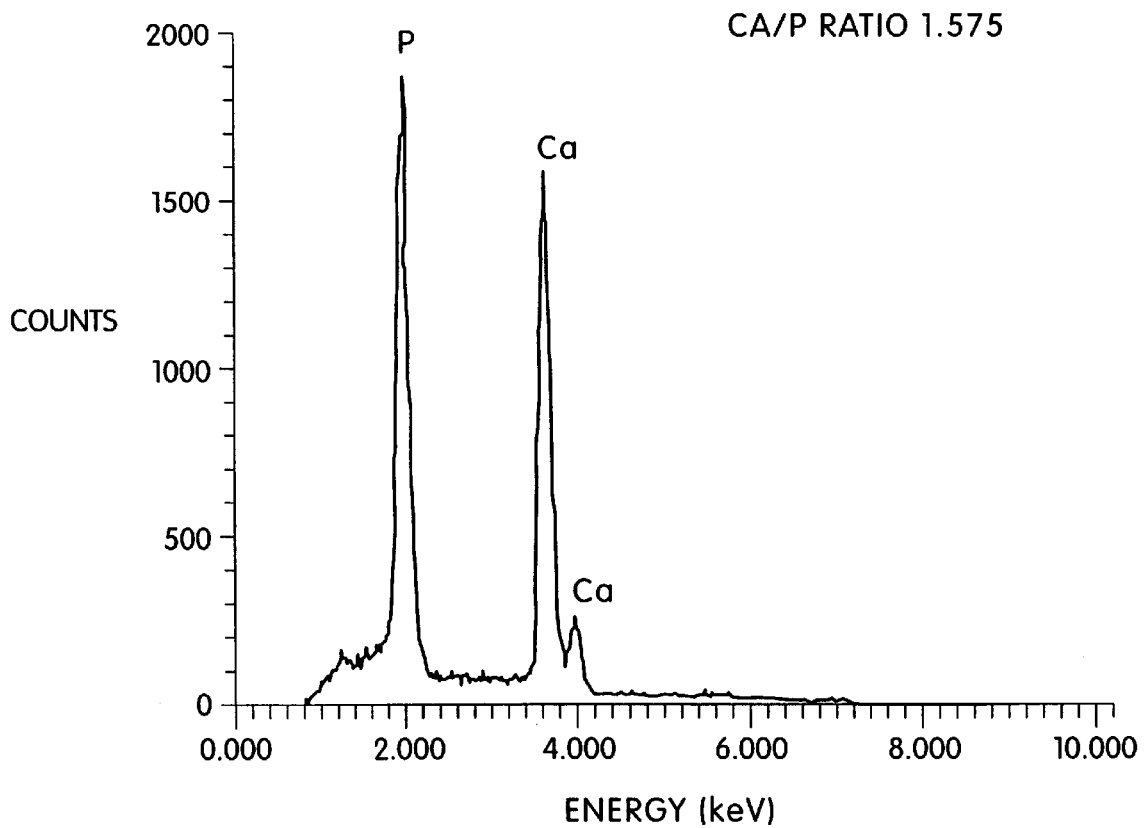
FIG. 2 is an energy-dispersive electron microprobe spectrum of the reactive amorphous calcium phosphate of the present invention after the vacuum heating procedure which yielded Ca/P to be 1.58.
Figure 4A:
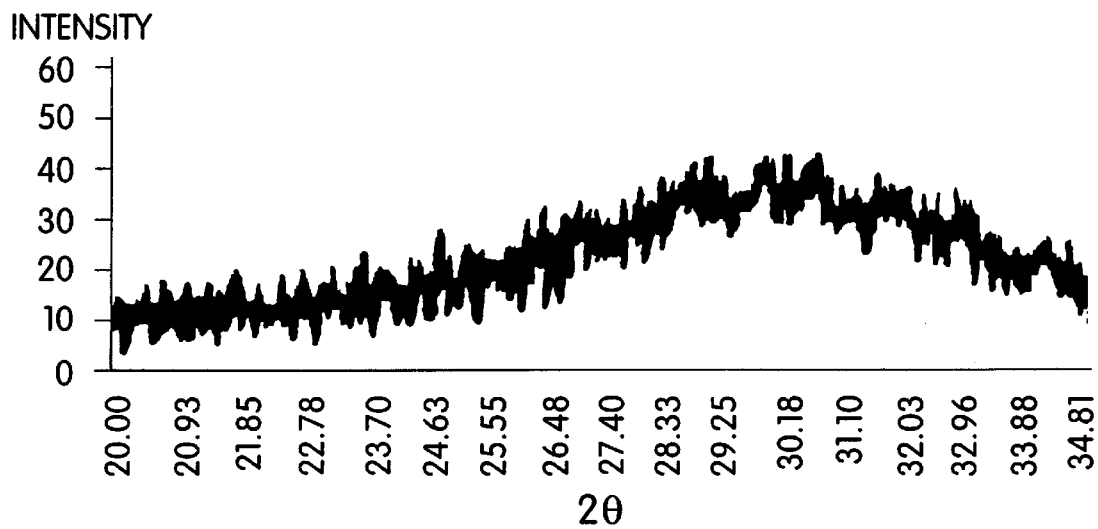
FIG. 4 are X-ray diffraction patterns of (a) reactive amorphous calcium phosphate; and (b) dicalcium diphosphate used in a reaction to form a bone substitute material of the invention.

The amorphous nature of the reactive ACP of the invention is characterized by an X-ray pattern that is devoid of sharp peaks at any position of the diffracting angles that correspond to known crystalline calcium phosphates (FIG. 4a). The Ca/P measurement performed using wave length-dispersive X-ray analysis on an electron micro-probe of the same material after heat treatment yields Ca/P to be 1.58 (FIG. 2).

These characterizations demonstrate that although there is a change in the local moiety of certain groups in the amorphous calcium phosphate solids, the overall amorphicity is maintained throughout the process.

In another preferred embodiment, the highly reactive amorphous calcium phosphate is reacted with a second calcium phosphate to obtain a PCA material. As discussed above, crystalline hydroxyapatite is the thermodynamically preferred reaction product, and is usually described as not resorbable under physiological conditions. The use of an amorphous calcium phosphate, which can convert quickly and completely to produce an apatitic compound without significant crystallization, provides a novel route to a poorly-crystalline apatitic calcium phosphate that is resorbable under physiological conditions.

The amorphous calcium phosphate powder of the present invention may be mixed with a promoter and may thereby convert to form a PCA material. This reaction may occur at room temperature upon mixing of the powder with any of a variety of both acidic and basic calcium phosphates in the presence of a limited amount of a fluid such as, but not limited to, water, saline, buffer solution, serum or tissue culture medium. Depending upon the amount of fluid added, the mixture of amorphous calcium phosphate of the present invention and a second calcium phosphate results in a highly formable and/or highly injectable paste with varying degrees of paste consistency.

Appropriate calcium phosphates for use as promoters with the ACP described herein include neutral, basic, and acidic calcium phosphates that provide the appropriate stoichiometry for reaction to obtain a apatitic calcium phosphate. In a preferred embodiment, an acidic (pH 5–7) calcium phosphate is used. Suitable calcium phosphates include, but are in no way limited to, calcium metaphosphate, dicalcium phosphate dihydrate, heptacalcium decaphosphate, tricalcium phosphates, calcium pyrophosphate dihydrate, the poorly crystalline apatitic material of the invention, calcium pyrophosphate, octacalcium phosphate, tetracalcium phosphate and additional ACPs. Other solids that would provide a source of phosphate or calcium, such as, by way of example only, CaO, $CaCO_3$, calcium acetate, and $H_3PO_4$, may be mixed to form a final product to yield a desired Ca/P ratio close to about 1.1–1.9, preferably about 1.3 to 1.5. It may be desirable to provide the second component in the amorphous or poorly crystalline state, as well.

Some calcium phosphate promoters may be prepared as either weak promoters or strong promoters. For instance, a DCPD sample with a grain size in the range of 100–125 $\mu$m (or distribution B3 in Example 5) reacts only marginally with the highly reactive ACP of the invention under certain conditions (see Example 5). DCPD of this grain size may be considered "weakly promoting". Thus, DCPD may be used in this format to screen for highly reactive ACPs.

Figure 4B:
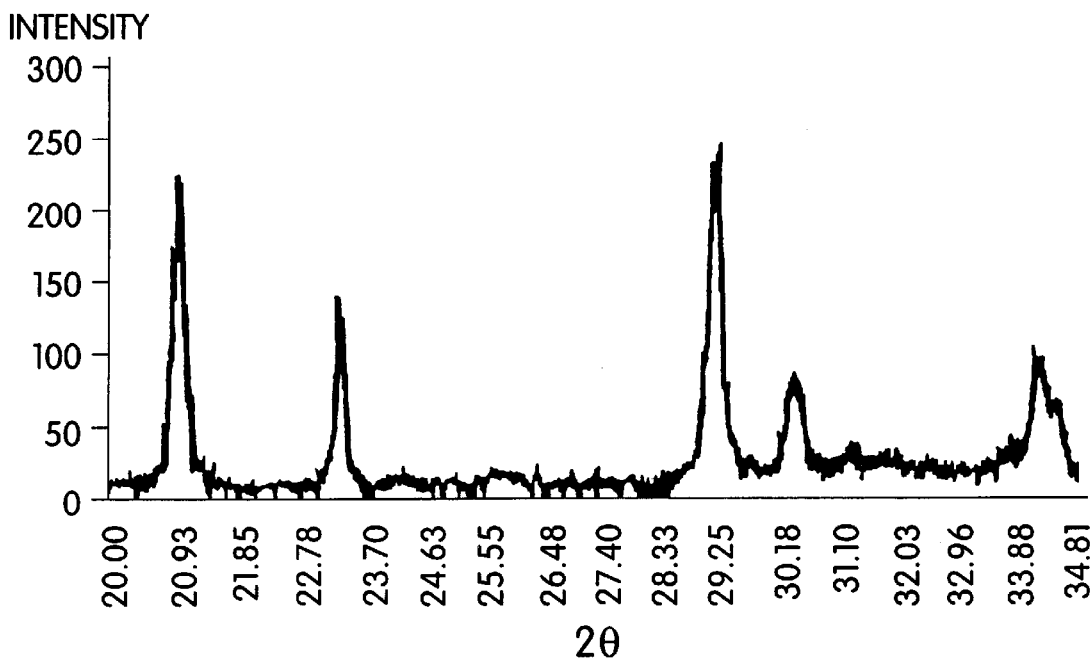

In some embodiments of the invention, it is not required that the reaction employ a participating second calcium phosphate to produce a PCA material. Rather, it is within the scope of the invention to merely promote hardening and the conversion of the reactive ACP into a PCA material by addition of one or more "passive" promoters (also termed "non-reactive" or "non-participatory" promoters) that do not participate in the reaction. Suitable passive promoters include, but are not limited to, materials or treatments that have previously been described as promoting conversion of calcium phosphate materials into hydroxyapatite. For example, water, heat, nucleators and catalysts can be used as passive promoters. In some embodiments, the catalysts provide surface area, the presence of which promotes the hardening and conversion of ACP to poorly crystalline apatitic calcium phosphate. For example, $Al_2O_3$, mica, glass and sand, among other things, are useful passive promoters. In preferred embodiments, material promoters are employed that are insoluble or of low solubility in water, may be prepared in granular form in the range of 1–200 $\mu$m in diameter and are resorbable in vivo. Thus, polymers such as poly L-lactic acid (PLLA) and polyglycolic acid (PGA) are particularly desirable promoters.

Where a second calcium phosphate is employed as a promoter, it is often crystalline, as is evidenced by the presence of sharp diffraction peaks typical to the calcium phosphate of interest in the X-ray diffraction pattern (FIG. 4b). In contrast, the reactive ACP is amorphous and shows no identifiable peaks by X-ray diffraction (FIG. 4a). Despite its higher crystallinity, however, X-ray diffraction suggests that dicalcium diphosphate is consumed in the reaction with reactive ACP and the product PCA material is of much reduced crystallinity. Similarly, when stoichiometric HA is employed as a second calcium phosphate source, it is also consumed in the reaction and a PCA material of reduced crystallinity is produced.

Because at least one of the reactants is amorphous and highly reactive, the formation reaction of the present invention proceeds at or above room temperature to provide a hardened apatitic material having a poorly-crystalline or microcrystalline microstructure. In preferred embodiments, the conversion reaction also is substantially complete, thereby insuring that all calcium and phosphate of the mixture are consumed by the resultant PCA product. This result permits reliable manufacture of apatitic products simply by selection of the relative proportions of the starting amorphous and secondary calcium phosphates. It is desirable to maintain a calcium to phosphate ratio of about 1.2–1.68, preferably less than 1.5, and most preferably about 1.38.

The product apatitic material contains labile environments characteristic of naturally-occurring bone. In naturally occurring bone, minerals are characterized by nanometer-sized structure, providing high surface areas to interact with the surrounding tissue environment, resulting in resorption and remodelling of tissues. The present invention, with its nanometer-sized crystals as the product, closely mimics the naturally occurring bone minerals. Further, properties such as crystallinity and Ca/P ratios are closely designed in the present invention to simulate the mineral properties found in living tissues of bone.

The PCA produced during the inventive reaction is associated with hardening of the hydrated precursor material. It should be noted, however, that while complete conversion of the ACP precursor is a preferred embodiment, hardening of the hydrated precursors may occur prior to complete conversion or even in the absence of complete conversion. Such partially converting, but nonetheless hardening, reactions are considered to be within the scope of the invention.

As mentioned above, combination of dry ACP with any other reactants and a limited amount of aqueous solution produces a hydrated precursor. By selecting the appropriate amount of liquid to be added to the reactants, the viscosity of the may be adjusted according to need. The hydrated precursor may be prepared either with an injectable or a formable consistency. Injectable consistency means as thick as possible while still capable of passing through a 16 to 18 gauge needle. Most often, this will be a "toothpaste"-like consistency. Formable refers to consistency that allows the material to retain its shape. In the extreme case of a formable consistency, the hydrated precursor will have the consistency of glazing putty or caulking compounds. The hydrated precursor also may be prepared with just enough liquid to be both injectable and formable. In the paste form, the material has markedly improved flow characteristics over prior art compositions. Flow characteristics are toothpaste-like while prior art materials generally exhibit a granular or oatmeal-like consistency. The hydrated precursor may be prepared before use, up to a period of several hours if held at room temperature and if evaporation is minimized. The storage time may be extended by maintaining the paste at reduced temperatures in the range of 1–10° C. in the refrigerator provided steps are taken to minimize evaporative loss.

In some preferred embodiments (e.g., Examples 9–14, below), the reaction is endothermic and occurs slowly at room temperature, but is accelerated significantly at body temperature. This is particularly useful in a surgical situation, since the paste formed by mixing reactants with water remains injectable for a considerable period of time (up to several hours) while held at or below room temperature. Thus, at room temperature (ca. 22° C.) the paste hardens after a time greater than one hour and remains formable and/or injectable for longer than 10 minutes, preferably longer than one hour, and most preferably longer than three hours. Following injection at the implant site (ca. 37° C.), the paste hardens in less than about an hour, preferably in about 10–30 minutes.

Composites and Additives

The delivery vehicles of the instant invention may be formed from the inventive PCA material alone or as composites between the PCA material and other substances. Composites may be desirable to change any number of physical parameters of the vehicle including but not limited to strength, resorption time, adherence, injectability, frictional characteristics, or therapeutic agent carrying capacity or release kinetics. In general, those practiced in the art of composite fabrication will understand the methods and concepts important in composite fabrication. Additional guidance for the preparation of PCA material composites may be obtained in co-pending United States patent application entitled "Bioresorbable Ceramic Composites", U.S. Ser. No. 08/729,354, filed on even date herewith and incorporated herein by reference.

In vitro Device Formation

In addition to surgical application in paste form, the inventive vehicles may be pre-formed outside the body, hardened, and implanted in the solid form. Pre-formed devices may be hand shaped, molded or machined. Loading of the therapeutic agent may be accomplished by addition of the agent directly to the buffer or vehicle used to prepare the hydrated precursor. Alternatively, after hardening, the vehicle may be exposed to the therapeutic agent using dipping, rolling or spray coat methods.

Biologically Active Agents

Any biologically useful agent may be delivered from the inventive delivery vehicle. In general, the only requirement is that the substance remain active in the presence of the vehicle during fabrication or be capable of being subsequently activated or re-activated. Since the inventive paste can be prepared with a large number of aqueous vehicles and substituents, those in the art will be familiar with which specific additives can be included in order to improve stability of the agent. The stability and/or compatibility of a particular agent with the inventive vehicle, as well as fabrication strategies, may be tested empirically in vitro. Specifically, the agent may be incorporated into the inventive vehicle by one or more of the of the methods described herein. Following hardening of the vehicle at 37° C., the substance may be leached from the device into an analysis medium such as water or an appropriate buffer and the compound collected from the vehicle by diffusion into the analysis medium. The analysis medium may then be analyzed for the presence of active agent. In some instances, the vehicle will be broken up, pulverized, or otherwise fragmented prior to contacting the analysis medium. Other methods of analysis that do not require agent diffusion, such as the growth of cells on the vehicle or other physical, chemical, or bio assays will be known to practitioners for specific compounds.

Biologically active agents useful in the practice of the present invention include any substance having biological activity, including organic molecules, proteins, peptides, nucleic acids, nucleoproteins, polysaccharides, glycoproteins, lipoproteins, and synthetic and biologically engineered analogs thereof. Also included are chemical agents that have biological effects (e.g., antibiotics, dyes, etc.). Proteins can be prepared by synthetic, biochemical, or recombinant techniques. Preferably, though not necessarily, the biologically active agent is one that has been deemed safe and effective for use by an appropriate governmental agency or body. For example, drugs approved for human use in the United States are listed by the Food and Drug Administration (FDA) under 21 C.F.R. §§ 330.5, 331–361, and 440–460; drugs approved for veterinary use in the United States are listed by the FDA under 21 C.F.R. §§ 500–582.

The term "biologically active agent" includes pharmacologically active substances that produce a local or systemic effect in animals, plants, or viruses. The term thus means any substance intended for use in the diagnosis, cure, mitigation, treatment or prevention of disease or in the enhancement of desirable physical or mental development and conditions in an animal, plant, or virus. The term "animal" used herein is taken to mean mammals, such as primates (including humans), sheep, horses, cattle, pigs, dogs, cats, rats, and mice; birds; reptiles; fish; insects; arachnids; protists (e.g. protozoa); and prokaryotic bacteria.

Classes of biologically active compounds that can be loaded into the delivery vehicle of the present invention include, but are not limited to, anti-AIDS substances, anti-cancer substances, antibiotics, ACE inhibitors, antigens adrenergic antagonists, antacids, immunosuppressants, anti-viral substances, enzyme inhibitors, neurotoxins, opioids, hypnotics, antihistamines, lubricants, tranquilizers, anti-convulsants, muscle relaxants and anti-Parkinson substances, anti-spasmodics and muscle contractants, anti-diarrheals, anti-emetics, laxatives, diuretics, miotics and anti-cholinergics, anti-glaucoma compounds, anti-parasite and/or anti-protozoal compounds, anti-hypertensives, analgesics, anti-pyretics, anti-inflammatory agents, anti-histamines, anti-tussive agents, anti-vertigo, antinertigic and anti-motion sickness medications, local anesthetics, ophthalmics, prostaglandins, anti-depressants, anti-psychotic substances, anti-emetics, imaging agents, specific targeting agents, trophic factors, growth factors, immunosuppressants, immunoactivators, anti-mitotics neurotransmitters, proteins, cell response modifiers, vaccines, nucleic acids, genes, gene fragments, gene regulatory sequences (such as promoters, enhancers, or other regulatory sites), antisense molecules, and other bioactive moieties or components of biosynthetic pathways.

A more complete listing of classes of compounds suitable for loading into delivery vehicles according to the present invention may be found in the *Pharnazeutische Wirkstoffe* (Von Kleemann et al. (eds), Stuttgart, N.Y., 1987), or in any of a variety of available pharmacology textbooks, such as *Lippincott's Illustrated Pharmacology Reviews* (Harvey et al. (eds), J. B. Lippincott Co., Philadelphia, 1992), or *Examination & Board Review Pharmacology* (Katzing et al., Appleton & Lange, Connecticut, 1993), each of which is incorporated herein by reference. Examples of particular biologically active substances are presented below:

Angiogenic factors are substances that stimulate the growth of vasculature and include compounds such as veg-f, and some growth factors and mitogens.

Anti-AIDS substances are substances used to treat or prevent Autoimmune Deficiency Syndrome (AIDS). Examples of such substances include CD4, 3'-azido-3'-deoxythymidine (AZT), 9-(2-hydroxyethoxymethyl)-guanine acyclovir( ), phosphonoformic acid, 1-adamantanamine, peptide T, and 2',3' dideoxycytidine.

Anti-cancer substances are substances used to treat or prevent cancer. Examples of such substances include anti-metabolites (such as, for example, methotrexate, fluorouracil, 5-fluorouracil, cytarabine, mercaptopurine, 6-mercaptopurine, 6-thioguanine), antibiotics (such as, for example, daunorubicin, doxorubicin), alkylating agents (such as for example, mechlorethamine, cyclophosphamide, uracil mustard, busulfan, carmustine, lomusline), mitotic spindle poisons (such as, for example, vinblastine, vincristine), hormones (such as, for example, hydroxyprogesterone, medroxyprogesterone acetate, magistral acetate, diethylstilbestrol, testosterone propionate, fluoxymesterone), and other agents (such as, for example, vindesine, hydroxyurea, procarbazine, aminoglutethimide, melphalan, chlorambucil, acarbazine (DTIC: dimethyltriazenomidazole carboxamide), cytosine arabinoxide).

Antibiotics are art recognized and are substances which inhibit the growth of or kill microorganisms. Antibiotics can be produced synthetically or by microorganisms. Examples of antibiotics include bactericidal agents, such as aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin. Antibiotics are sometimes provided in insoluble form, which can be used where delayed delivery is desired.

Anti-viral agents are substances capable of destroying or suppressing the replication of viruses. Examples of anti-viral agents include a-methyl-P-adamantane methylamine, 1,-D-ribofufranosyl-1,2,4-triazole-3 carboxamide, 9-[2-hydroxyethoxy]methylguanine, adamantanamine, 5-iodo-2'-deoxyuridine, trifluorothymidine, interferon, and adenine arabinoside. Particular agents useful in the treatment of herpes viruses include acyclovir, vidarabine, idoxuridine, and ganciclovir.

Enzyme inhibitors are substances which inhibit an enzymatic reaction. Examples of enzyme inhibitors include edrophonium chloride, N-methylphysostigmine, neostigmine bromide, physostigmine sulfate, tacrine HCl, tacrine,1-hydroxy maleate, iodotubercidin, p-bromotetramisole, 10-(alpha-diethylaminopropionyl)-phenothiazine hydrochloride, calmidazolium chloride, hemicholinium-3, 3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine HCl, hydralazine HCl, clorgyline HCl, deprenyl HCl,L(−)-, deprenyl HCl,D(+)-, hydroxylamine HCl, iproniazid phosphate, 6-MeO-tetrahydro-9H-pyrido-indole, nialamide, pargyline HCl, quinacrine HCl, semicarbazide HCl, tranylcypromine HCl, N,N-diethylaminoethyl-2,2-diphenylvalerate hydrochloride, 3-isobutyl-1-methylxanthne, papaverine HCl, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate,R(+)-, p-aminoglutethimide tartrate,S(−)-, 3-iodotyrosine, alpha-methyltyrosine,L-, alpha-methyltyrosine,D L-, acetazolamide, dichlorphenamide, 6-hydroxy-2-benzothiazolesulfonamide, and allopurinol.

Neurotoxins are substances which have a toxic effect through their action on the nervous system, e.g. nerve cells. Neurotoxins include adrenergic neurotoxins, cholinergic neurotoxins, dopaminergic neurotoxins, calcium channel blockers, and other neurotoxins. Examples of adrenergic neurotoxins include N-(2-chloroethyl)-N-ethyl-2-bromobenzylamine hydrochloride. Examples of cholinergic neurotoxins include acetylethylcholine mustard hydrochloride. Examples of dopaminergic neurotoxins include 6-hydroxydopamine Br, 1-methyl-4-(2-methylphenyl)-1,2,3,6-tetrahydro-pyridine hydrochloride, 1-methyl-4-phenyl-2,3-dihydropyridinium perchlorate, N-methyl-4-phenyl-1,2,5,6-tetrahydropyridine HCl, 1-methyl-4-phenylpyridinium iodide. Examples of calcium channel blockers include $\Omega$-conatoxin and verapamil.

Opioids are substances having opiate like effects that are not derived from opium. Opioids include opioid agonists and opioid antagonists. Opioid agonists include codeine sulfate, fentanyl citrate, hydrocodone bitartrate, loperamide HCl, morphine sulfate, noscapine, norcodeine, normorphine, thebaine. Opioid antagonists include norbinaltorphimine HCl, buprenorphine, chlornaltrexamine 2HCl, funaltrexamione HCl, nalbuphine HCl, nalorphine HCl, naloxone HCl, naloxonazine, naltrexone HCl, and naltrindole HCl.

Hypnotics are substances which produce a hypnotic effect. Hypnotics include pentobarbital sodium, phenobarbital, secobarbital, thiopental and mixtures, thereof, heterocyclic hypnotics, dioxopiperidines, glutarimides, diethyl isovaleramide, a-bromoisovaleryl urea, urethanes and disulfanes.

Antihistamines are substances which competitively inhibit the effects of histamines. Examples include pyrilamine, chlorpheniramine, tetrahydrazoline, and the like.

Lubricants are substances that increase the lubricity of the environment into which they are delivered. Examples of biologically active lubricants include water and saline.

Tranquilizers are substances which provide a tranquilizing effect. Examples of tranquilizers include chloropromazine, promazine, fluphenzaine, reserpine, deserpidine, and meprobamate.

Anti-convulsants are substances which have an effect of preventing, reducing, or eliminating convulsions. Examples of such agents include primidone, phenytoin, valproate, Chk and ethosuximide.

Anti-inflammatories are compounds that inhibit inflammation. Different types of anti-inflammatory drugs block different chemical mediators. Examples of anti-inflammatory agents include nonsteroidal anti-inflammatory drugs (NSAIDS), such as aspirin, phenylbutazone, indomethacin, sulindac, tolmetin, ibuprofen, piroxicam, fenamates, which have anti-inflammatory, analgesic, and antipyretic activities. Also included are non-narcotic analgesics such as acetaminophen and phenacetin, although the anti-inflammatory activity of these drugs is weaker. Certain slow-acting anti-inflammatories, such as gold salts, chloroquine, D-Penicillamine, and methotrexate are useful in the treatment of arthritis. Gout-specific anti-inflammatories include colchicine, allopurinol, probenecid, and sulfinpyrazone.

Muscle relaxants and anti-Parkinson agents are agents which relax muscles or reduce or eliminate symptoms associated with Parkinson's disease. Examples of such agents include mephenesin, methocarbomal, cyclobenzaprine hydrochloride, trihexylphenidyl hydrochloride, levodopa/carbidopa, and biperiden.

Anti-spasmodics and muscle contractants are substances capable of preventing or relieving muscle spasms or contractions. Examples of such agents include atropine, scopolamine, oxyphenonium, and papaverine.

Miotics and anti-cholinergics are compounds which cause bronchodilation. Examples include echothiophate, pilocarpine, physostigmine salicylate, diisopropylfluorophosphate, epinephrine, neostigmine, carbachol, methacholine, bethanechol, and the like.

Anti-glaucoma compounds include betaxalol, pilocarpine, timolol, timolol salts, and combinations of timolol, and/or its salts, with pilocarpine.

Anti-parasitic, -protozoal and -fungals include ivermectin, pyrimethamine, trisulfapyrimidine, clindamycin, amphotericin B, nystatin, flucytosine, ketocanazol, fluconazole, natamycin, miconazole, metronidazole, diloxanide furoate, paromomycin, chlorquine, emetine, dehydroemetine, sodium stibogluconate, (for leishmaniasis), melarsoprol (for trypanosomiasis), nifurtimox (for trypanosomiasis), suramin (for trypanosomiasis), pentamidone (for trypanosomiasis), and anti-malarial agents (such as, for example, primaquine, chloroquine, quinine, mefloquine, pyrimethamine, and chlorquanide).

Anti-hypertensives are substances capable of counteracting high blood pressure. Examples of such substances include alpha-methyldopa and the pivaloyloxyethyl ester of alpha-methyldopa.

Analgesics are substances capable of preventing, reducing, or relieving pain and Anti-pyretics are substances capable of relieving or reducing fever. Examples of such substances include aspirin, phenybutazone, idomethacin, sulindac, tolmetic, ibuprofen, piroxicam, fenamates, acetaminophen, phenacetin, morphine sulfate, codeine sulfate, meperidine, and nalorphine.

Local anesthetics are substances which have an anesthetic effect in a localized region. Examples of such anesthetics include procaine, lidocain, tetracaine and dibucaine.

Ophthalmics include diagnostic agents such as sodium fluorescein, rose bengal, methacholine, adrenaline, cocaine, and atropine. Ophthalmic surgical additives include alpha-chymotrypsin and hyaluronidase.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Anti-psychotic substances are substances which modify psychotic behavior. Examples of such agents include phenothiazines, butyrophenones and thioxanthenes.

Anti-emetics are substances which prevent or alleviate nausea or vomiting. An example of such a substance includes dramamine.

Imaging agents are agents capable of imaging a desired site, e.g. tumor, in vivo. Examples of imaging agents include substances having a label which is detectable in vivo, e.g. antibodies attached to fluorescent labels. The term antibody includes whole antibodies or fragments thereof.

Specific targeting agents include agents capable of delivering a therapeutic agent to a desired site, e.g. tumor, and providing a therapeutic effect. Examples of targeting agents include agents which can carry toxins or other agents which provide beneficial effects. The targeting agent can be an antibody linked to a toxin, e.g. ricin A or an antibody linked to a drug.

Neurotransmitters are substances which are released from a neuron on excitation and travel to either inhibit or excite a target cell. Examples of neurotransmitters include dopamine, serotonin, γ-aminobutyric acid, norepinephrine, histamine, acetylcholine, and epinephrine.

Trophic factors, growth factors, and cell response modifiers are factors whose continued presence improves the viability or longevity of a cell. In some cases, they produce chemotactic effects, or have protective effects against toxins or neurotoxins, or against neurodegeneration. Suitable such factors include, but are not limited to, platelet-derived growth factor (PDGP), neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor, glial derived growth neurotrophic factor, ciliary neurotrophic factor, nerve growth factor, and bone growth/cartilage-inducing factor (alpha and beta), or other bone morphogenetic proteins.

Other cell response modifiers are the interleukins, interleukin inhibitors or interleukin receptors, including interleukin 1 through interleukin 10; interferons, including alpha, beta and gamma; hematopoietic factors, including erythropoietin, granulocyte colony stimulating factor, macrophage colony stimulating factor and granulocyte-macrophage colony stimulating factor; tumor necrosis factors, including alpha and beta; transforming growth factors (beta), including beta-1, beta-2, beta-3, inhibin, and activin; and bone morphogenetic proteins such as OP-1, BMP-2 and BMP-7.

Hormones include estrogens (such as, for example, estradiol, estrone, estriol, diethylstibestrol, quinestrol, chlorotrianisene, ethinyl estradiol, mestranol), anti-estrogens (such as, for example, clomiphene, tamoxifen), progestins (such as, for example, medroxyprogesterone, norethindrone, hydroxyprogesterone, norgestrel), anti-progestin (mifepristone), androgens (such as, for example, testosterone cypionate, fluoxymesterone, danazol, testolactone), and anti-androgens (such as, for example, cyproterone acetate, flutamide). Hormones are commonly employed in hormone replacement therapy and/or for purposes of birth control. Steroid hormones, such as prednisone, are also used as immunosuppressants and anti-inflammatories. Delivery of steroid hormones can be delayed by esterification. Thyroid hormones include triiodothyronne, thyroxine, propylthiouracil, methimazole, and iodixode. Pituitary hormones include corticotropin, sumutotropin, oxytocin, and vasopressin.

Nucleic acids are molecules, including DNA or RNA molecules, that comprise one or more nucleosides and/or nucleotides. Since calcium compounds are known to promote cell transfection and DNA uptake in some systems, it is anticipated that resorption of the present delivery device may improve transfection efficiency. Nucleic acid molecules can be delivered as vaccines or, for example, as antisense agents. Alternatively, DNA molecules can be prepared for use in gene therapy, in which molecules can correct or compensate for genetic errors in cells into which the DNA molecules are to be introduced.

Standard protocols and regimens for delivery of the above-listed agents are known in the art. Typically, these protocols are based on oral or intravenous delivery. To the extent that the present invention provides for alternate delivery modes, modification to these protocols may be appropriate.

Biologically active agents are introduced into the delivery vehicle of the present invention during or after its formation (see Examples 20–21). Agents may conveniently be mixed into the paste prior to setting. Alternatively, the vehicle may be shaped and hardened and then exposed to the therapeutic agent in solution. This particular approach is particularly well suited for proteins, which are known to have an affinity for apatitic materials. A buffer solution containing the biologically active agent may be employed, instead of water, as the aqueous solution in which the amorphous calcium phosphate is converted into the synthetic, poorly crystalline apatitic material of the present invention. Buffers may be used in any pH range, but most often will be used in the range of 5.0 to 8.0 in preferred embodiments the pH will be compatible with prolonged stability and efficacy of the desired therapeutic agent and, in most preferred embodiments, will be in the range of 5.5 to 7.4. Suitable buffers include, but are not limited to, carbonates, phosphates (e.g., phosphate buffered saline), and organic buffers such as Tris, HEPES, and MOPS. Most often, the buffer will be selected for it's biocompatibility with the host tissues and its compatibility with the therapeutic agent. For most applications of nucleic acids, peptides or antibiotics a simple phosphate buffered saline will suffice.

Biologically active agents are introduced into the vehicle in amounts that allow delivery of an appropriate dosage of the agent to the implant site. In most cases, dosages are determined using guidelines known to practitioners and applicable to the particular agent in question. It is generally preferred, for those agents that bind to a receptor, to achieve local levels approximately 1–2 fold higher than the dissociation constant of the receptor-agent complex. Loading levels, device size, and resorption properties can be determined empirically through the use of animal models and human efficacy studies, as is common in the pharmaceutical industry.

One of the advantages of the present delivery material, as compared with ceramic devices generally, and with calcium phosphate materials in particular, is that it can be formed under mild reaction conditions. For example, although calcium phosphate-based ceramics (e.g., hydroxyapatites) have been much studied as potential drug delivery materials because of their biocompatibility and known affinity for protein agents, such materials are typically prepared in processes that require have detrimental effects on many therapeutic agents. For example, some methods require sintering above 500° C., others require the use of acidic conditions, and still others require extended periods of time to grow crystals containing the therapeutic agent. By contrast, the present synthetic PCA drug delivery vehicle can be prepared at ambient temperatures and physiologically relevant pHs (see Example 4). Accordingly, a wide variety of biologically active materials that might be destroyed during the preparation of standard calcium phosphate materials can be incorporated into the drug delivery material of the present invention. Protein agents in particular are often sensitive to heat and other unfavorable conditions; the present synthetic PCA material therefore constitutes a particularly improved delivery system for protein agents.

Modification of Delivery Kinetics

One advantage of the delivery system of the present invention is that the rate of resorption of the delivery vehicle can be modulated through modifications in the preparative methods. Specifically, methods that lead to a more dense hardened product will generally result in a slower resorption time of the pure inventive PCA calcium phosphate in vivo. In this regard, there are a variety of ways to alter the density or resorption kinetics of the hardened product. These include adjustment of the volume of liquid used to create the paste, alteration of grain size of the starting materials, and compression of the paste during hardening. Composites, in which leachable or biodegradable particles or materials are incorporated into the paste, and ultimately the hardened PCA material, may also be prepared. The leachable or biodegradable materials may subsequently be removed (e.g., by leaching) from the hardened material in vivo, so that a highly porous implant is produced. Additionally, the inventive PCA material may be prepared with a distribution of densities within the same implant. One way this may be accomplished is by preparing in vitro-hardened PCA material of one density, pulverizing the hardened material to a desired grain size, and then mixing the pulverized material with a second PCA material paste designed to produce a different density PCA material. PCA materials made in this way will resorb asynchronously.

The use of overall smaller grain size material to prepare the PCA material precursor powder results in a longer time to resorb and/or reossify in vivo (see Examples 5 and 19). Since the ACP precursor is generally prepared at a very small grain size, when two components are used to produce the inventive vehicle, the grain size of the other non-ACP component is generally used to adjust resorption time. In this regard, the grain size may be adjusted by using a ground and sieved second component to select a specific grain size distribution for addition to the final mixture. In another embodiment, the second component is ground with the ACP for varying amounts of time to affect the resorption rate.

Composite materials with altered resorbability kinetics are produced by incorporating into the device an "erosion rate modifier", which is a material whose presence alters the rate of resorbability of the device as a whole. Erosion rate modifiers that increase the rate at which the drug delivery device resorbs include any leachable or biodegradable compound that affects the solubility (e.g., by altering the porosity) of the device over time in vivo. Erosion rate modifiers that decrease the rate at which the drug delivery device resorbs include crystalline calcium phosphates, particularly hydroxyapatite, and diphosphate compounds.

Implant Sites

The delivery vehicle of the present invention can be used to deliver biologically active agents to any of a variety of sites in a body, preferably in a human body though veterinary applications are also within the scope of the invention. The delivery vehicle may also be employed to accomplish in vitro delivery of a biologically active agent.

The delivery vehicle of the present invention offers the advantage of controlled, localized delivery. As is well known, smaller amounts of biologically active agent are required when the agent is delivered to a specific site rather than administered systemically. Furthermore, potential toxic side effects of the agent are minimized when the agent is delivered from the delivery vehicle of the present invention. Also, the agent's activity is maximized because it is protected within the delivery vehicle until it is delivered to its site.

Figure 9:
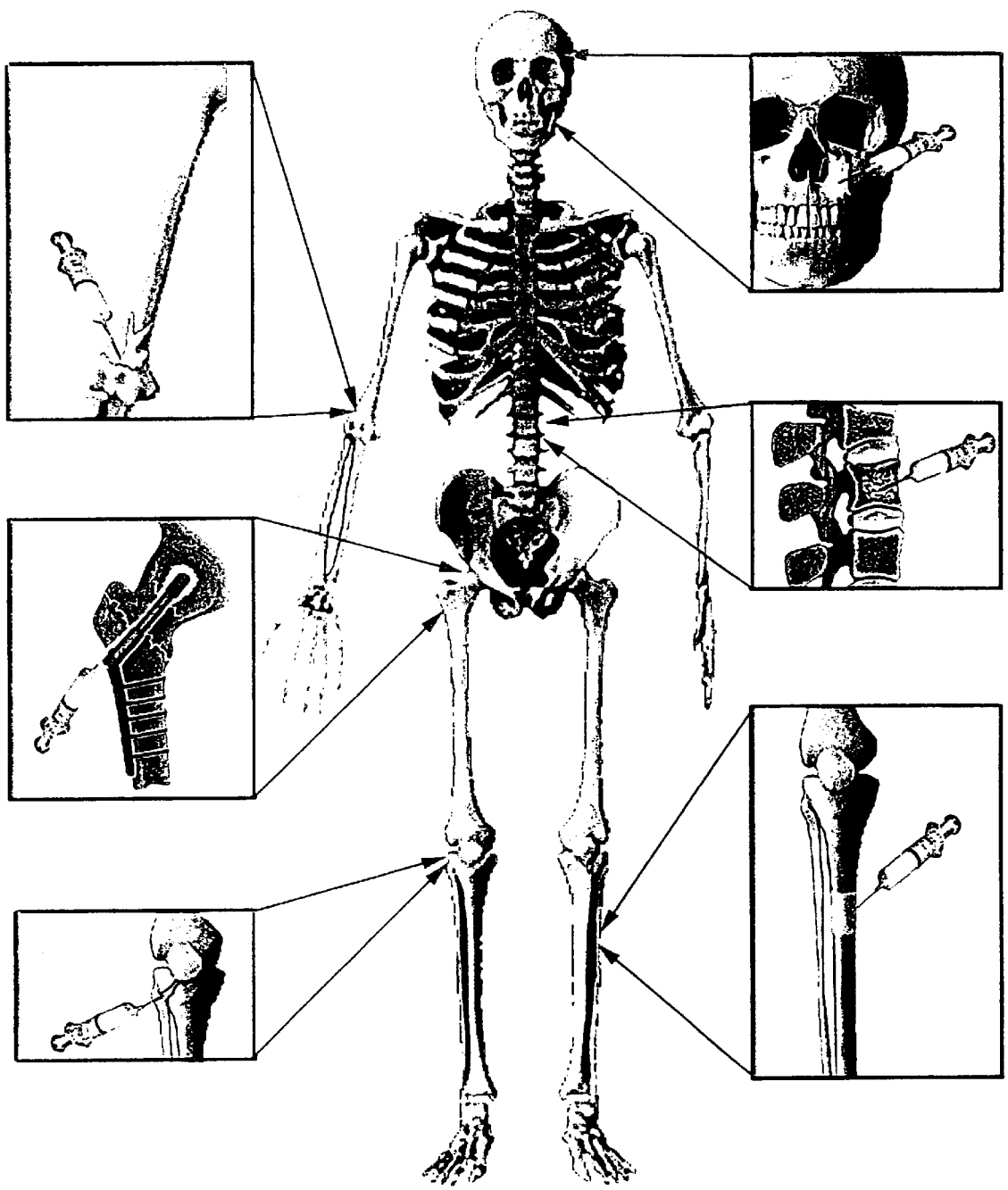
FIG. 9 depicts use of the delivery vehicle of the present invention in a variety of bony sites.

The delivery vehicle of the present invention can be injected or implanted into any acceptable tissue. Oral formulations are also considered within the scope of the invention. Preferred delivery sites include sites in bone, muscle, the spinal cord, the central nervous system, the interperitoneal cavity, subcutaneous locations, and the vitreous and aqueous humor of the eye. When the delivery vehicle is delivered to a site under circumstances where vehicle migration is a concern, anchoring sutures or hooks may be incorporated into the vehicle so that it can be attached and maintained in position. When appropriate, the delivery vehicle may be anchored by insertion into a bony site (see below). Particular applications and preferred delivery sites are discussed in more detail below:

Bone: The delivery vehicle of the present invention has particular advantages for delivery of biologically active agents to sites in bone. Implantation of a delivery vehicle of the present invention in a bony site may alternatively or additionally be utilized to anchor a delivery vehicle and accomplish systemic drug delivery, or may be utilized to accomplish delivery to a site adjacent to, though not strictly speaking "within", the bone. FIG. 9 depicts many useful applications of the delivery vehicle of the present invention in bony sites.

Naturally-occurring bone mineral is made of nanometer-sized, poorly-crystalline calcium phosphate with apatitic structure. However, unlike the ideal stoichiometric crystalline hydroxyapatite, $Ca_{10}(PO_4)_6(OH)_2$, with atomic Ca/P ratio of 1.67, the composition of bone mineral is significantly different and may be represented by the following formulae, $Ca_{8.3} (PO_4)_{4.3} (HPO_4,CO_3)_{1.7} (OH, CO_3)_{0.3}$.

Bone mineral non-stoichiometry is primarily due to the presence of divalent ions, such as $CO_3^{2-}$ and $HPO_4^{2-}$, which are substituted for the trivalent $PO_4^{3-}$ ions. Substitution by $HPO_4^{2-}$ and $CO_3^{2-}$ ions produces a change of the Ca/P ratio, resulting in Ca/P ratio which may vary between 1.50 to 1.70, depending on the age and bony site. Generally, the Ca/P ratio increases during aging of bone, suggesting that the amount of carbonate species typically increases for older bones. It is the Ca/P ratio in conjunction with nanocrystalline size and the poorly-crystalline nature that yields specific solubility property of the bone minerals. And because bone tissues undergo constant tissue repair regulated by the mineral-resorbing cells (osteoclasts) and mineral-producing cells (osteoblasts), solubility behavior of minerals is important in maintaining a delicate metabolic balance between these cells activities.

The drug delivery material of the present invention is a nano-size, poorly crystalline solid with a Ca/P ratio comparable to that of natural bone minerals. The material is bioresorbable, can be produced at low temperatures, and is readily formable and injectable. For all of these reasons, the inventive material is particularly well suited for drug delivery in bony sites. Furthermore, this synthetic PCA material can support bone growth so that it is eventually replaced by the patient's own bone. It should be borne in mind, however, that bone ingrowth may well affect the resorbability rate of the drug delivery material of the present invention. Accordingly, it may be desirable in certain circumstances (e.g., where the biologically active agent must be delivered according to a precise, predetermined administrative schedule) to reduced bone growth into the drug delivery vehicle, for example by blocking penetration of osteocytic or chondrocytic cells or precursors. In most circumstances, ossification can be avoided by placing the device at some distance away from bone. Generally, 1 mm will be sufficient, although greater distances are preferred. Also, compounds such as Indian hedgehog gene and gene products, parathyroid hormone-related protein (PTHRP) and PTHRP receptor agonists may be included in, on, or adjacent to the drug delivery device in order prevent bone growth.

In other circumstances, such bone ingrowth can desirably be encouraged. As shown in Examples 14, 17, and 18, the PCA calcium phosphate material can be placed into bony sites and allowed to resorb in a manner that results in its apparent complete (100%) replacement with new bone. Where optimal ossification is desired, the devices and objects may be seeded with bone forming cells (see, for example, U.S. application entitled "Cell Seeding of Ceramic Compositions", filed on even date herewith and incorporated herein by reference). This goal is most easily accomplished by placing the device in contact with a source of the patient's own bone forming cells. Such cells may be found in bone tissue or in bone-associated blood or fluids, including exogenous fluids which have been in contact with bone or bone materials or regions, including the periosteum, cancellous bone or marrow. In the case of devices such as screws and pins, the introduction of which into bone is accompanied by bleeding, no further seeding is required. For plates, which oppose only cortical bone, induction of a periosteal lesion which will contact the device is recommended. In yet other embodiments, it will be useful to surgically prepare a seating within the bone by removing a portion of cortical bone at the implant site. Other steps may also be taken to augment ossification, including introduction bone forming cells harvested from the patient into the graft, or incorporation of trophic factors or bone growth inducing proteins into, or onto the device. Non-autologous bone cells are also within the scope of the invention if the desired amount of bone regeneration occurs prior to host rejection of the bone forming cells. In this regard, immunosuppressants may be administered to the device recipient, in some cases by incorporation into the device. Thus, cells or tissues obtained from primary sources, cell lines or cell banks may all be useful in certain embodiments.

Certain categories of biologically active agents are expected to be particularly suitable for delivery to bony sites. For example, where the drug delivery vehicle is applied to a damaged bone site, it may be desirable to incorporate bone regenerative proteins (BRPs) into the vehicle. BRPs have been demonstrated to increase the rate of bone growth and to accelerate bone healing (see, for example, Appel et al., *Exp. Opin. Ther. Patents* 4:1461, 1994). Exemplary BRPs include, but are in no way limited to, Transforming Growth Factor-Beta (TGF-β), Cell-Attachment Factors (CAFs), Endothelial Growth Factors (EGFs), OP-1, and Bone Morphogenetic Proteins (BMPs). Such BRPs are currently being developed by Genetics Institute, Cambridge, Mass.; Genentech, Palo Alto, Calif.; and Creative Biomolecules, Hopkinton, Mass. Bone regenerative proteins and trophic factors can also be used to stimulate ectopic bone formation if desired. The inventive PCA material containing BMP-7 can be placed subcutaneously, and bone formation will occur within 1–2 months.

Antibiotics and antiseptics are also desirably delivered to bony sites using the PCA drug delivery vehicle of the present invention. For example, one of the major clinical implications arising from bone-graft surgery is a need to control the post-operative inflammation or infection, particularly infection associated with osteomyelitis. An embodiment drug delivery device of the present invention, including an antibiotic, could be used as (or in conjunction with) an improved bone graft to reduce the chances of local infection at the surgery site, contributing to infection-free, thus faster, bone healing process. The efficacy of antibiotics is further enhanced by controlling the resorption of the poorly crystalline hydroxyapatite such that it dissolves at a rate that delivers antibiotic peptides or its active component at the most effective dosage to the tissue repair site. Exemplary antibiotics include, but are in no way limited to, penicillin, tetracycline, kanamycin, gentamycin, chlortetracycline hydrochloride (aureomycin), minocyline, dosycycline, vanomycin, bacitracin, neomycin, erythromycin, streptomyan, cephalosporins, chloramphenicol, oxytetracycline (terramycine), and derivatives thereof. Antibiotics and bone regenerating proteins may be incorporated together into the PCA material of the present invention, to locally deliver most or all of the components necessary to facilitate optimum conditions for bone tissue repair.

Other biologically active agents that are desirably delivered to bony sites include anti-cancer agents, for example for treatment of bone tumors (see, for example, Otsuka et al., *J. Pharm. Sci.* 84:733, 1995). The drug delivery vehicle of the present invention is particularly useful, for example, where a patient has had a bone tumor surgically removed because the synthetic, PCA material of the present invention can improve the mechanical integrity of the bone site while also treating any remaining cancer cells to avoid metastasis. Exemplary anti-cancer agents include, for example, methotrexate, cisplatin, prednisone, hydroxyprogesterone, medroxyprogesterone acetate, megestrol acetate, diethylstilbestrol, testosterone propionate, fluoxymesterone, vinblastine, vincristine, vindesine, daunorubicin, doxorubicin, hydroxyurea, procarbazine, aminoglutethimide, mechlorethamine, cyclophosphamide, melphalan, uracil mustard, chlorambucil, busulfan, carmustine, lomusline, dacarbazine (DTIC: dimethyltriazenomidazole carboxamide), fluorouracil, 5-fluorouracil, cytarabine, cytosine arabinoxide, mercaptopurine, 6-mercaptopurine, thioguanine.

Additional biologically active agents that can desirably be incorporated into the synthetic PCA drug delivery system of the present invention for delivery to bony sites are agents that relieve osteoporosis. For example, amidated salmon calcitonin has been demonstrated to be effective against osteoporosis.

Vitamin D and Vitamin K are also desirably delivered to bony sites, as are angiogenic factors such as veg f, which can be used when it is desirable to increase vascularization.

Subcutaneous implant sites

Application of the present drug delivery device is not limited to bony sites, of course. In non-bony sites, the device is known resorb without ossification.

Placement of the instant delivery device subcutaneously is particularly useful for more systemic administration of biologically active compounds. The administration of estrogens and/or progesterones for the used in fertility control is an example of a subcutaneous application. Additionally, the administration of antigens and/or vaccines may be accomplished through subcutaneous implantation.

Central nervous system

The delivery of therapeutic substances to the central nervous system may be accomplished with the inventive delivery vehicles. Useful therapeutic substances include the delivery of γ-aminobutyric acid to epileptic foci, the delivery of L-dopa or dopamine in the striatum or substantia nigra for the treatment of Parldnson's disease, the delivery of growth factors for the prevention of neural degeneration such as GDNF in the lateral ventricles, striatum or substantia nigra for the treatment of Parkinson's disease, the administration of NGF to cortical and other regions for the treatment of Alzheimer's disease, or the administration of CNTF to the sacral or lumbar spinal cord for the treatment of amyelolateral sclerosis.

Other

Other potential delivery sites include intramuscular, interperitoneal, and occular areas.

EXAMPLE

Example 1

Preparation of Reactive Amorphous Calcium Phosphate

This example describes the step-by-step preparation and methods to render relatively inert amorphous calcium phosphate solids into a highly reactive amorphous calcium phosphate of the present invention.

Solution A was prepared at room temperature by the rapid dissolution of 55 g $Na_2HPO_4 \cdot 7H_2O$ (sodium phosphate), 50 g NaOH (sodium hydroxide), 30 g $NaHCO_3$, (sodium bicarbonate) and 2 g $Na_4P_2O_7 \cdot 10H_2O$ in 1.3 l of distilled water. Solution B was prepared at room temperature by rapid dissolution of 43 g $Ca(NO_3)_2 \cdot 4H_2O$ (calcium nitrate tetrahydrate) and 1 g $MgCl_2 \cdot 6H_2O$ in 0.5 l of distilled water.

The inert carbonated amorphous calcium phosphate was then prepared at room temperature by the rapid addition of solution B to rapidly stirring solution A. The precipitate of gel-like amorphous calcium phosphate thus formed was immediately filtered using filter paper (0.05 sq. m) with medium filter speed and a vacuum pressure of about $10^{-2}$ torr. The material formed a thin cake and was washed with approximately 4 liters of distilled water by adding water into the filtrating funnel. The washed material was then collected using spatula and immersed into a liquid nitrogen in a 2.5 L container. Following the formation of hard frozen pieces, the container was transferred into a vacuum chamber for 24 hrs ($10^{-1}$–$10^{-2}$ torr), until a fine and dry powder was obtained.

Although the procedure described above may be performed at room temperature, the entire process preferably takes place below ambient temperature (4–5° C.), so as to further prevent the amorphous state from converting into more stable crystalline form. Further, such elements or ions known to act as inhibitors of crystalline hydroxyapatite formation may be added into the solution in trace amounts.

An infrared spectrum of the inert amorphous material at this point in the process contains peaks characteristic of P—O groups (600 and 1000 $cm^{-1}$), $CO_3^{2-}$ group (1,420–1,450 $cm^{-1}$) with relatively large peak of O—H group (~3,550 $cm^{-1}$). X-ray diffraction pattern of the same material show amorphous nature of the material as demonstrated by absence of any sharp peaks when the measurement of crystallinity is determined by taking ratio of coherent peaks to background.

The inert amorphous material described above was then made into a reactive form by heating for 60 minutes at 450° C. (±3° C.). The IR of the heated material (not shown) shows reduction of particular O—H and $CO_3^{2-}$ groups, indicating significant reduction of $H_2O$ and $CO_3^{2-}$ as $CO_2$ and $H_2O$. In similarly prepared samples the carbon content was observed to drop approximately 60% with a total carbonate ratio decreasing from 1.56% to 0.5%. Note, however, that the amorphous nature of the material was not lost during this process, as demonstrated by the X-ray diffraction pattern shown in FIG. 4(a). The Ca/P ratio measurement of this material after the heat treatment was determined to be 1.575, using a method of quantitative electron microprobe analysis (FIG. 2). The overall morphological and ultrastructural properties of amorphous material is shown in FIG. 1, as seen under a transmission electron microscope. Note the "amorphous" appearance of the material with absence of sharp edges separating each granules with certain portion of the material to exhibit shapeless form (arrows). An extremely high specific surface area of 120 $m^2/g$, with an average pore size of approximately 130 Å was observed in this material.

Example 2

Preparation of Reactive Amorphous Calcium Phosphate

The preparation was conducted as described in Example 1 above, with the exception that the preparation of Solutions A and B was replaced by the following reactions. Solution A was prepared at room temperature by the rapid dissolution of 90.68 g of $Ca(NO_3)_2 \cdot 4H_2O$ in 1.2 liter of carbonated distilled $H_2O$. Solution B was prepared by dissolving 40.57 g of $K_2HPO_4$ in 1.53 liters of distilled $H_2O$, containing 24 ml of 45 vol. % KOH solution. Chemical and physical properties of the product amorphous calcium phosphate resulting from this procedure were similar to those of the material prepared accordingly for Example 1.

Example 3

Preparation of Reactive Amorphous Calcium Phosphate

The preparation was conducted as described in Example 1 above, with the exception that the preparation of Solutions A and B were replaced by the following reactions. Solution A was prepared at room temperature by the rapid dissolution of 10.58 g of $Ca(NO_3)_2.6H_2O$ in 0.15 liters of carbonated distilled $H_2O$ at pH greater than 9.0, as adjusted by NaOH. Solution B was prepared by dissolving 7.8 g of $(NH_4)_2HPO_4$ in 0.35 liters of distilled $H_2O$. Chemical and physical properties of the product amorphous calcium phosphate resulting from this procedure were similar to those of the material prepared according to Examples 1 and 2.

Example 4

Preparation of Synthetic Poorly Crystalline Apatitic Drug Delivery Material from Reactive Amorphous Calcium Phosphate This example describes the preparation of drug delivery vehicle material of the invention.

The dicalcium phosphate dihydrate (DCPD) used in this example was prepared in the following manner. Solution A was prepared at room temperature by rapid dissolution of 10 g $H_9N_2O_4P$ (diammonium hydrogen phosphate) in 500 ml distilled water at a pH of 4.6–4.8. Solution B was prepared at room temperature by the rapid dissolution of 17.1 g $Ca(NO_3)_2.4H_2O$ (calcium nitrate tetrahydrate) in 250 ml distilled water. The dicalcium phosphate dihydrate was prepared at room temperature by the rapid addition of solution B to the stirring solution A. Immediately thereafter, the sample was filtered using filter paper (0.05 sq. m) with medium filter speed and a vacuum pressure of about $10^{-2}$ torr. The material formed a thin cake which was washed with about 2 liters of distilled water and then air dried at room temperature for 24–72 hrs.

The reactive amorphous calcium phosphate material prepared from Example 1 was physically dry-mixed with dicalcium phosphate dihydrate ($CaHPO_4.2H_2O$) at 50:50 wt % using a mortar and pestle for 3–5 min. Water (1 ml/g of mixed material) was then added to the powder mixture to yield a paste-like consistency. The amount of $H_2O$ added varied, depending on whether a thick or thin paste was desired. The paste material was then wrapped in moist tissue paper and was hardened into a solid mass by heating 37° C. The hardening process could be delayed for several hours by wrapping the sample in parafilm and holding it at 4° C. Also, hardening can be allowed to proceed at ambient temperature, although setup times may then be expanded.

The hardened material was composed of nanometer-sized, poorly crystalline apatitic calcium phosphate with an inherent solubility property that exceeded reported solubilities for a synthetic hydroxyapatite material. This is demonstrated in FIG. 3, where the concentration of calcium ions released into a controlled pH buffer solution over 24 hrs at 37° C., was significantly higher for the PCA material of the present invention (curve 50) than the standard crystalline hydroxyapatite material (curve 52).

Example 5

Preparation of Synthetic, Poorly Crystalline Apatitic Drug Delivery Material from Precursors of Selected Particle Size This example demonstrates the preparation of synthetic PCA drug delivery vehicle materials using precursors having a selected particle size.

DCPD was prepared as described in Example 4. The dry material was ground for 5 minutes in a SPEX 8510 laboratory mill with a SPEX 8505 alumina ceramic grinding chamber. Following grinding the material was serially sieved through a Tyler test sieve shaker to produce DCPD with 8 different grain size distributions as indicated in Table 1.

TABLE 1

Figure 8:
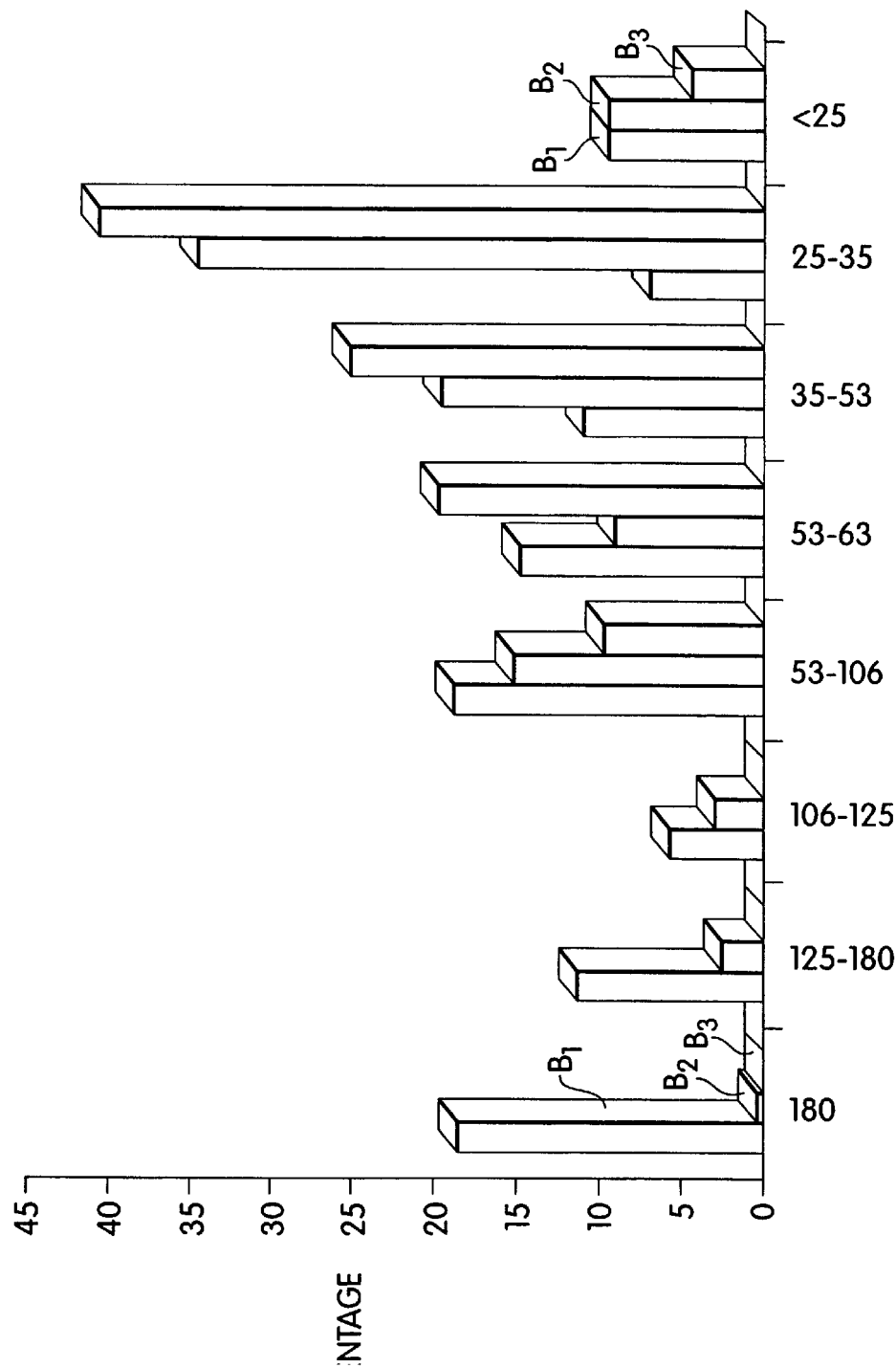
FIG. 8 is a bar graph displaying particle size distribution for various formulations described in Example 5.

| DCPD Grains size distribution | |
|---|---|
| Sample | Grain Size Distribution |
| 1 | <25 µm |
| 2 | 25–35 µm |
| 3 | 35–53 µm |
| 4 | 53–63 µm |
| 5 | distribution B3 (FIG. 8) |
| 6 | 106–125 µm |
| 7 | distribution B2 (FIG. 8) |
| 8 | unsieved distribution B1 (FIG. 8) |

The reactive amorphous calcium phosphate material prepared from Examples 1, 2, or 3 was physically dry-mixed 1:1 (wt/wt) with DCPD for 10 minutes using a SPEX 8510 laboratory mill with a SPEX 8505 alumina ceramic grinding chamber. Water (1.0–0.8 ml/gm of dry mix) was then added to the powder mixture to yield a paste-like consistency. 5 of the 8 samples indicated in Table 1 hardened well in 30 minutes at 37° C. Samples 6, 7 and 8 did not harden as quickly or as firmly as the other samples. Each of these samples had significantly higher percentages of >100 µm particles than did the other samples.

Example 6

Preparation of Synthetic PCA Drug Delivery Material from Reactive Amorphous Calcium Phosphate Reactive amorphous calcium phosphate material as prepared in Examples 1 was dry-mixed with other calcium phosphate compounds, according to the method described in Example 4. These compounds included, but were not limited to: $Ca(PO_3)_2$ (calcium metaphosphates), $Ca_7(P_5O_{16})_2$ (heptacalcium decaphosphate), $Ca_2P_2O_7$ (calcium pyrophosphate), $Ca_3(PO_4)_2$ (tricalcium phosphates). The dry-mixture ratio was properly calculated to be between Ca/P ratios of 1.5–1.70, depending on the molar Ca/P ratio of the compound mixed with the reactive amorphous calcium. The resulting material was poorly crystalline apatitic calcium phosphate solids with solubility properties same as shown in FIG. 3.

Example 7

Preparation of an Injectable Paste for Formation of a Synthetic, PCA Material from a Reactive, Amorphous Calcium Phosphate This example describes the preparation of an injectable paste for the formation of poorly crystalline apatitic calcium phosphate solid.

The dried mixed materials prepared according to Examples 4 or 6 were mixed with distilled $H_2O$ (2.3 ml/g). A paste was formed that could be easily shaped by hand or injected through a nozzle as small as 0.5 mm ID. The flowability increased after refrigerating the paste at 4° C. for 2–3 hrs.

The material could be stored in a paste form for about 12 hours at 4° C. in an air tight container without hardening.

Example 8

Characteristics of a Synthetic Poorly Crystalline Apatitic Calcium Phosphate

The crystalline content of the PCA material was determined by X-ray diffraction and I-R spectrometry.

FIGS. 5a–d are the X-ray diffraction spectra of the reaction product between DCPD and the reactive amorphous calcium phosphate as described in Example 4. The reaction mixture was placed in a moist environment at 37° C. and examined by X-ray diffraction spectrometry at different times. X-ray scan conditions were (a) copper anode, (b) γ=1.4540598 Å, and (c) a scan range 20–35° at a step of 0.02° and step interval of 2 seconds. FIG. 6 shows the infrared spectra of dicalcium phosphate dihydrate (a), the activated ACP of the invention (b), and the PCA material of the present invention (c).

Figure 5A:
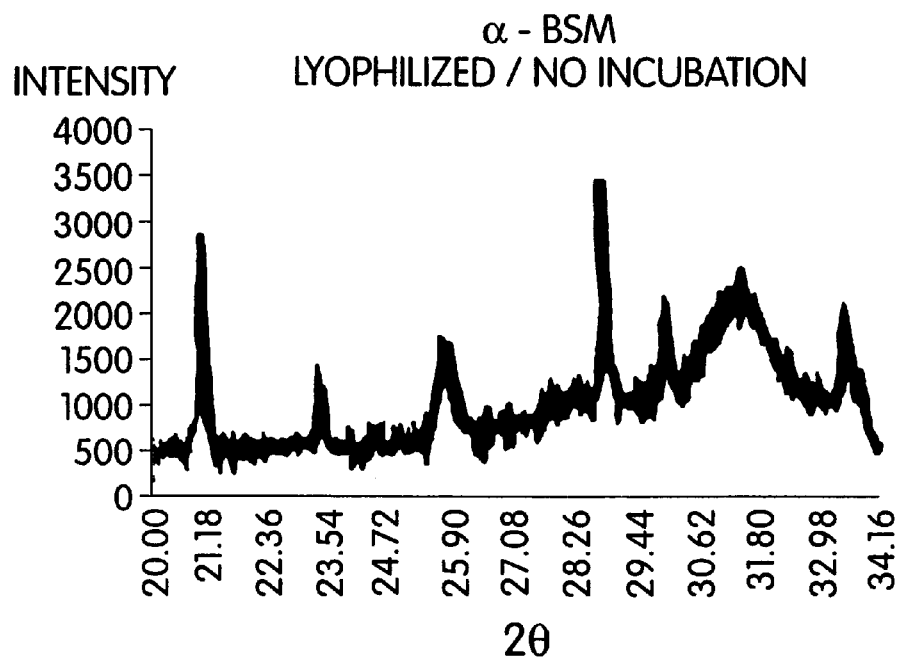
FIGS. 5a–d are X-ray diffraction patterns tracking the progress of the reaction of a mixture of reactive amorphous calcium phosphate and dicalcium diphosphate to form a PCA material of the present invention.
Figure 5B:
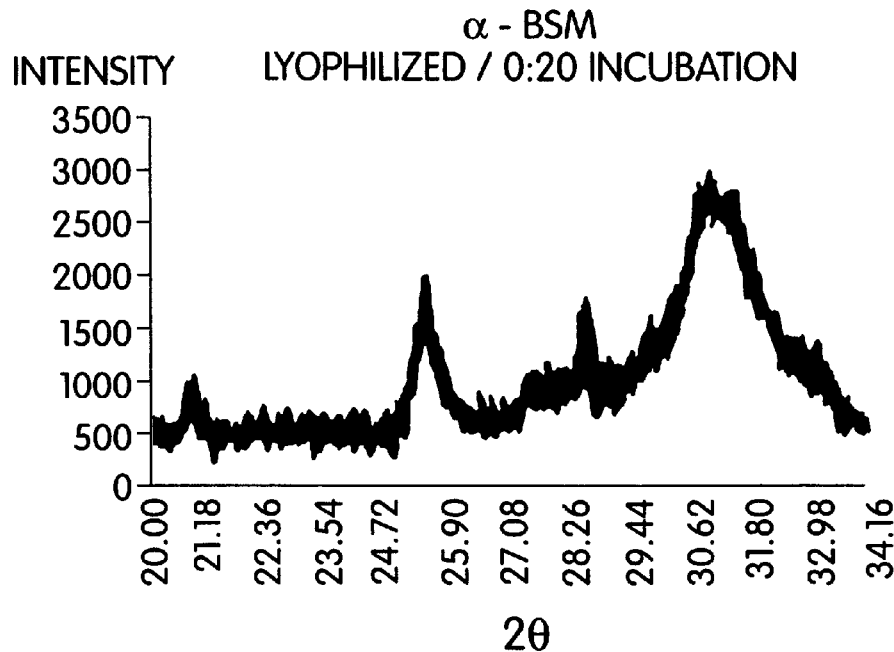
Figure 5C:
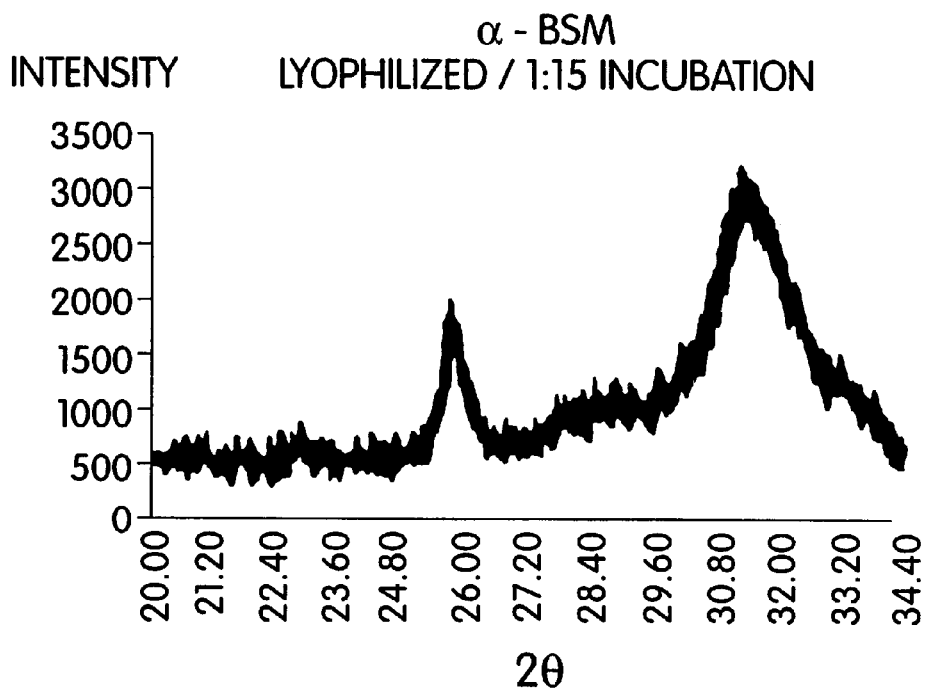
Figure 5D:
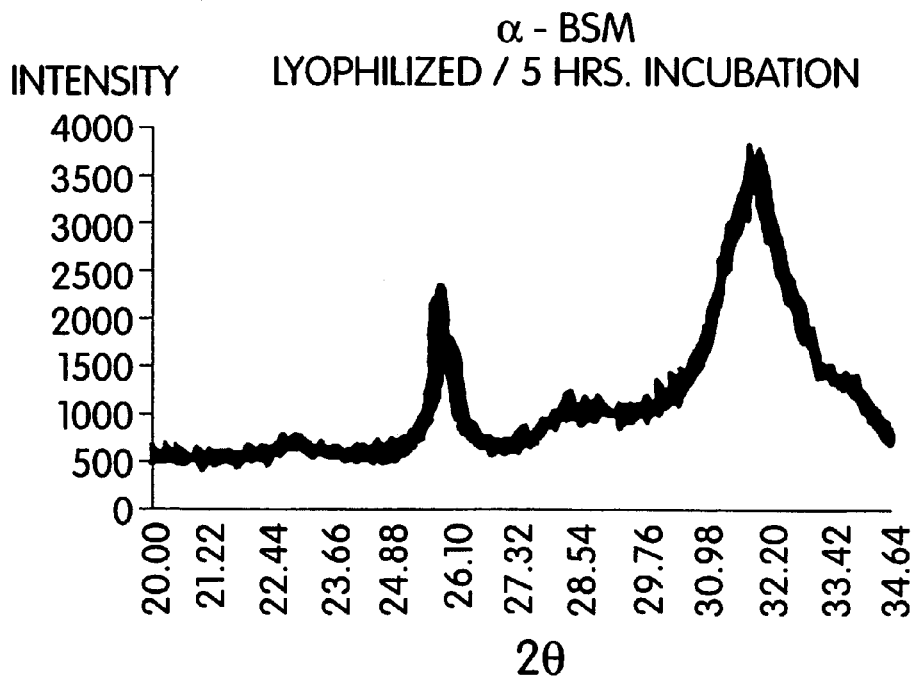
Figure 6A:
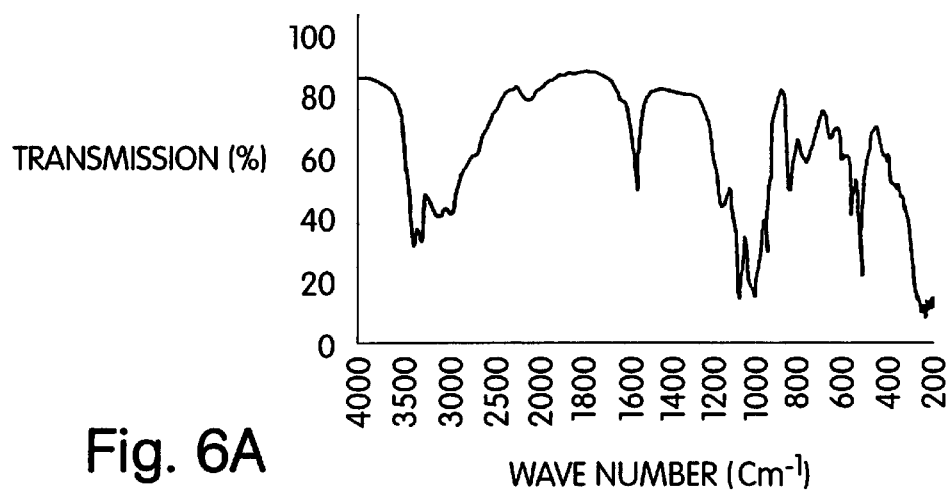
FIG. 6 is infrared spectra of (a) dicalcium phosphate dihydrate, (b) the activated ACP of the invention, and (c) the PCA material of the present invention.
Figure 6B:
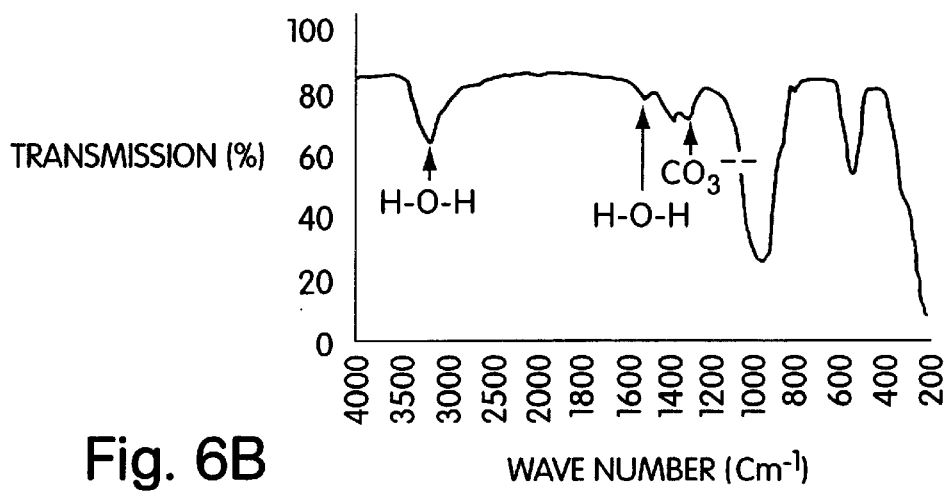
Figure 6C:
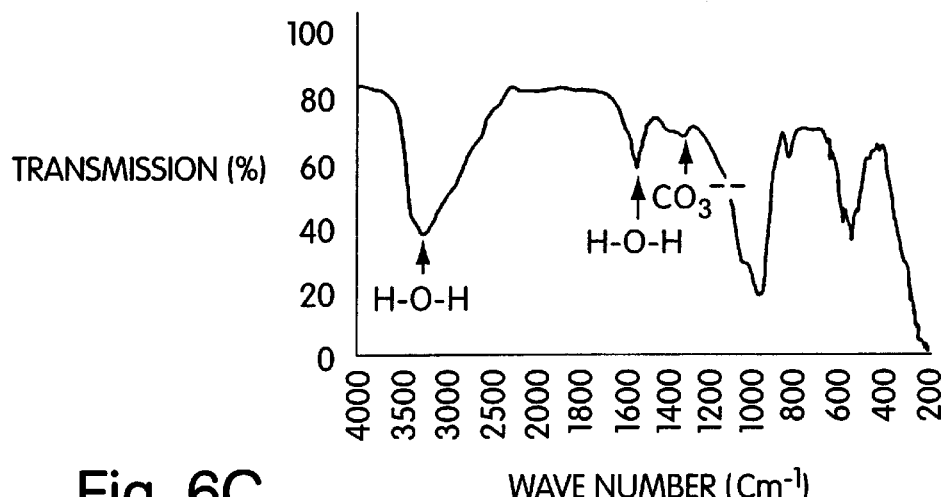
Figure 7:
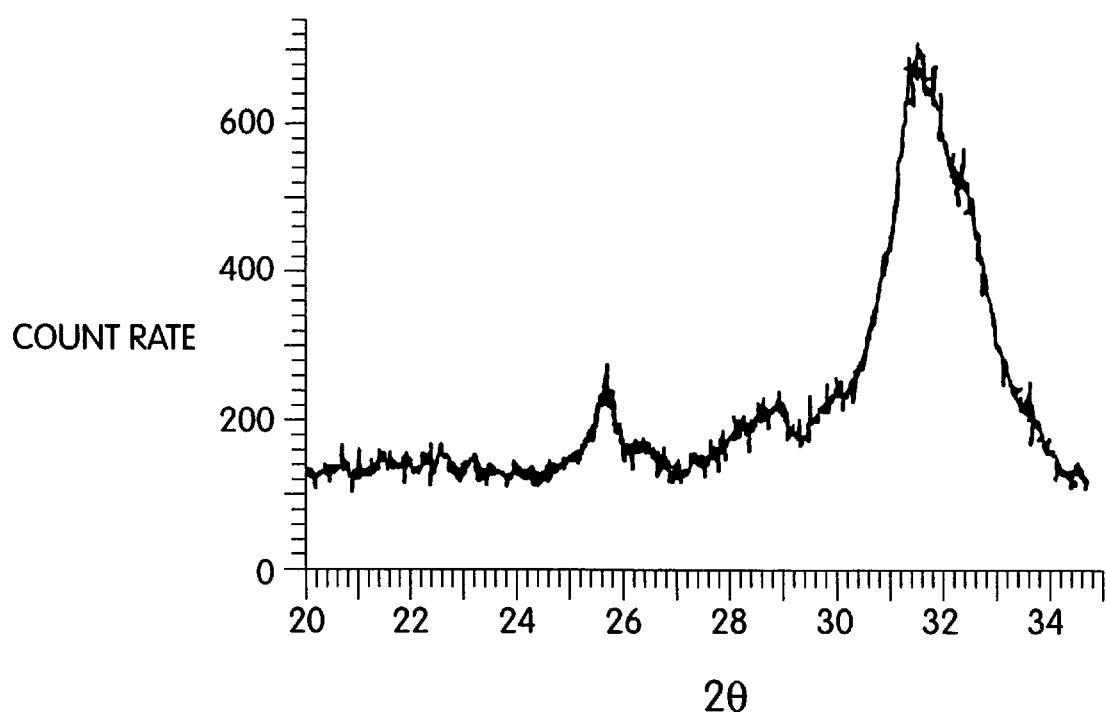
FIG. 7 is an X-ray diffraction pattern of naturally occurring bone.

Samples of FIGS. 5a–5d were incubated for 0,20 min, 75 min and 5 hours, respectively. The samples were removed at the noted time and lyophilized to preserve chemical characteristics. FIG. 5a, taken at the start of the reaction, represents a combination of peaks attributable to the starting ACP and dicalcium diphosphate (see, FIG. 4 for component XRD patterns). The sharp peaks at ca. 20.25°, 23.5°, 29.5°, 30.75° and 34.2° for crystalline dicalcium diphosphate are readily observed. With increase in reaction time, the sharp crystalline peaks subside and wide (amorphous) peaks appear centered at 26°, 28.5°, 32.0° and 33.0°. It is interesting to note that there is no significant change in the spectra after 75 minutes of reaction, indicating that the conversion reaction was essentially complete in little more than one hour. The X-ray diffraction pattern of the PCA material of the invention (FIG. 5d) can be compared to that of naturally occurring bone, shown in FIG. 7. The two spectra are nearly identical, indicating the close biomimetry of the apatitic calcium phosphate of the invention.

Example 9–12

Characteristics of Injectable Paste for Formation of Synthetic PCA Material from a Reactive, Amorphous Calcium Phosphate These examples demonstrate the effect of fluid volume on the consistency and reactivity of injectable paste to be used in the formation of a synthetic, poorly crystalline hydroxyapatite material. Each of the pastes were prepared as described in Example 7, above, and the consistency and rate of reaction at room temperature and 37° C. were determined. Observations are reported in Table 2.

TABLE 2

Formability, injectability and reactivity of one gram drug delivery vehicle material prepared with variable water volume

| Example No. | water volume (mL) | formability | injectability | hardening time (min) (4 *C/RT/37° C.) |
|---|---|---|---|---|
| 9 | 0.7 | – crumbles | – | –/–/– |
| 10 | 0.8* | +++ easily formed paste | + | >60/>60/30 |
| 11 | 0.9* | ++ toothpaste | ++ | >60/>60/30 |
| 12 | 1.0 | + liquid toothpaste | +++ | >60/>60/30 |

*Under some circumstances (e.g., evaporation) these samples may dry out somewhat over a period of one hour at room temperature. In such cases, additional water may be added to restore the original consistency.

Example 13

Infrared Spectra of Precursor and Product Materials

This example compares the infrared spectra of crystalline and amorphous precursors produced according to the Examples and the final PCA material produced by reacting similar precursors. FIG. 7a presents the IR spectrum of brushite (DCPD) prepared as described in Example 4; FIG. 7b presents the spectrum of ACP after heat treatment, prepared as described in Example 1; and FIG. 7c is the IR spectrum of the PCA material prepared as described in Example 4.

Example 14

Implantation and Resorption of Drug Delivery Vehicle in a Bony Site

The purpose of this study was to assay resorption and ossification of PCA calcium phosphate in a bony implant site. The method is also useful for testing the resorption and ossification properties of PCA calcium phosphate formulations and composites of the invention.

The test article used was a PCA calcium phosphate formulation prepared as described in Example 4. The ACP and DCPD were mixed in the specified proportions and ground for 1 minute, 30 seconds in the SPEX grinder equipment.

Adult (>5 month old) NZW male rabbits were held in quarantine and acclimatized for a minimum of 10 days prior to the initiation of the study. Animals were individually housed in suspended stainless steel cages. Wood shavings were used in dropping pans under the cages. Prior to initiation of the study, animals were assigned to groups or treatments randomly and were identified by a numbered ear tattoo and by a corresponding cage card. All animals had single defects placed in one tibia. Timepoints for evaluations were 2, 4, and 8 weeks (2 animals at each timepoint). Surgery was performed under full anesthesia and aseptic surgical conditions.

After obtaining adequate anesthesia (e.g., ketamine/xylazine to effect), using aseptic technique, an incision was made over the lateral proximal tibia. The soft tissue was deflected away and the bone exposed. Using an approximately 5 mm trephine in a low speed dental handpiece with irrigation (0.9% physiologic saline) as needed, a ~5.5 mm diameter hole was cut through the cortical portion of the bone. The bony disk was dissected free from the cortex and the site was prepared for implantation. The hydrated precursor material in paste form was placed into the defect. Defects in control animals were left untreated. The soft tissues were then closed in layers. One sample per animal was prepared using this method.

Clinical observations of the animals' general health and well-being, with special regard to their ambulatory abilities, were made at least weekly. All animals appeared to be in good health. At the end of the study the animals were euthanized with an overdose of anesthetic and the implant site collected. Radiographs of the tibiae were made at scheduled intervals including after surgery and at the time of necropsy.

The implantation sites were fixed in formalin and stained with either hematoxylin and eosin, Masson's trichrome, or Von Kossa stained slides from decalcified samples. Undecalcified histological samples were also prepared and stained with light green basic fuschin. Slides were microscopically evaluated by a board certified veterinary pathologist (ACVP) with experience in laboratory animal pathology. Subjective observations were made of bone morphology, and presence or absence of organized bone and of detectable PCA calcium phosphate material was noted.

Figure 10A:
In FIG. 10a, the small arrows indicate one edge of the defect; the large arrowhead is at the yet unbridged defect.
Figure 10B:
In FIG. 10b, large arrowheads denote one edge of the defect. In both FIGS., magnification is 4×, bone is decalcified, and slides are treated with hematoxylin and eosin.

Histological results indicated some mineralization at 2 weeks. By 4–6 weeks, animals receiving implants had normal trabecular bone at the implant site with no evidence of remaining PCA calcium phosphate. The untreated controls had not fully healed in that they had less than full ingrowth and/or had non-cortical-type bone. FIGS. 10a and 10b are photomicrographs of untreated and treated tibia defects, respectively, 2 weeks after surgery. As can be seen, bone to the right of the defect edge in the untreated sample (FIG. 9a) is thin trabecular bone; new bone to the right of the defect edge in the treated sample is thick trabecular bone.

Example 15

Implantation and Resorption of Drug Delivery Vehicle in a Subcutaneous Site

This example demonstrates the resorption of the inventive PCA calcium phosphate when implanted subcutaneously into rats. It also demonstrates a useful screening procedure to test resorption characteristics of new formulations of bioceramic implant materials and composites.

Eighty male and eighty female Sprague-Dawley rats were each implanted with 4 ml (2–4 gm) of the inventive PCA (prepared according to Example 4) into the dorsal subcutis (>10× the amount considered maximal in humans on a per kg basis). Control animals were treated with an equal volume of saline. Operation procedures are described in Example 16. The rats were sacrificed according to the schedule presented below in Table 3; the implant site was examined as described in Example 16.

TABLE 3

Sacrifice Schedule

| Sacrifice Timepoint | PCA calcium phosphate implant |
|---|---|
| 1 week | 5 m/5 f |
| 2 weeks | 5 m/5 f |
| 1 month | 5 m/5 f |
| 3 months | 5 m/5 f |
| 1 year | 20 m/20 f |

Blood for clinical pathology analyses was collected via retroorbital sinus or cardiac puncture (all by the same method) while the animals were under $CO_2$ anesthesia. Blood samples were collected from each group of animals prior to scheduled sacrifice. Clinical observations of the animals for general health and well-being were performed at least weekly until 3 months, and then monthly.

At 1 week PCA material was present at the implant site and was found associated with moderate to marked granulomas presumable associated with the resorption process. At week two a small amount of PCA material was still present at the implant site and associated granulomas were mild to moderate. By week four most tissue appeared normal with a few mild granulomas persisting at the implant site. At week twelve no evidence of the implant remained.

Example 16

Implantation and Resorption of Drug Delivery Vehicle in an Intramuscular Site

This example describes the preparation of delivery vehicles that have varied in vivo resorption times as a result of varied grinding times. Individual dry precursors, ACP and DCPD were prepared as described in Example 4. Several different formulations of DCPD and ACP were then prepared by i) grinding DCPD for 15 sec, 30 sec, 1 min, 2.5 min, or 5 min in a SPEX grinder; ii) combining the ground DCPD 1:1 with ACP; and iii) grinding the mixture for an additional 15 sec, 30 sec, 1 min, 2.5 min, or 5 min, respectively. Total grinding times for the different preparations were therefore 30 sec, 1 min, 2 min, 5 min, and 10 min.

The PCA calcium phosphate, sterilized in powder form by approximately 2.5 Mrad of gamma irradiation, was prepared as described in Example 4 by taking the material in powder form and mixing with sterile water or saline and forming it into approximately 1 cm disks 2 mm thick and incubated for a minimum of 30 minutes at 37° C. Disks were implanted into adult male New Zealand White Rabbits immediately following fabrication.

Animals were assigned to dose groups which contained 3 males for a total of 15 animals. The implants were assigned to the rabbits randomly. 10–15 minutes prior to the surgery, the animal was premedicated with xylazine (10 mg/kg, i.m.). The animal was then given ketamine (50 mg/kg, i.m.). The dorsal surface of the animal was clipped free of hair and washed with a betadine surgical solution and alcohol. Before the surgery the animal was monitored to be sure that is was properly anesthetized. To do this, pressure was applied to the foot pad. When there was no response, the animal was properly anesthetized. Throughout the procedure, the animal was monitored for whisker twitching and the toe-pinch reflect, which indicated that the animal was not waking up.

Using aseptic technique and a scalpel blade, an incision 1–2 cm in length was made in the skin over the m. longissimus lumborum (which lies along both sides of the spine). When the incision was made, the underlying fascia and muscle was also cut to allow the sample to pas into the muscle. The sample disk was placed directly into the muscle, being sure that the entire implant was embedded in the muscle. The muscle was closed with a single absorbable suture and the skin was stitched closed subcutaneously. Metal skin staples were used to close the external skin surface incision. Five samples were placed on each side in this manner. Each sample was placed at the end of the incision and they were approximately 1 cm apart from each other (see diagram). The samples were in the form of 7 mm by 2 mm disks weighing approximately 150 mg. The animals were monitored and were given buprenorphine (0.02–0.05 mg/jg, s.q) upon awakening. The analgesic was administered 2 times per day for three days after surgery.

The animals were radiographed immediately after the surgery and for every two weeks thereafter. The radiographs were compared to track the resorption of the materials. A standardized method was used for the radiographs to minimize any variation between timepoints.

After euthanasia, implant sites were first evaluated by gross examination. In those sites with visible implants, the implants appeared as grey to yellow solid discs. In those sites where the implant had been resorbed, areas of red to tan discoloration of the muscle were observed.

Muscle tissue, with the implants, was removed, being careful not to disturb the implants. The tissues and the identifying marks were placed into labeled jars filled with 10% neutral buffered formalin. All implant sites were processed and evaluated microscopically. Observations included focal fibrosis, focal granulomatous inflammation, and appearance of the implant (in some cases). Fibrosis were primarily seen as fibrocytes and collagen. Animals with gross resorption had fibrosis and minimal to moderate granulomatous focal inflammation. Granulomatous inflammation was seen as focal aggregates of macrophages and giant cells, often with intracytoplasmic crystals, and occasional heterophils and lymphocytes. Inflammation around the non-resorbed implants was primarily minimal to mild and/or granulomatous inflammation, both of which are within the acceptable range for intramuscular implants.

At four weeks, the pellets made from PCA calcium phosphate implants that had been prepared by grinding for 30 seconds, 1 minute, or 2 minutes were fully resorbed. Those that had been prepared by grinding for 5 minutes or 10 minutes were not fully resorbed.

Example 17

Implantation and Resorption of Drug Delivery Vehicle in a Bony Site

The purpose of this study was to assay resorption and ossification of the PCA calcium phosphate of the invention in a bony site.

Mature (>1 year) beagle dogs were employed for this study because of their size and historical use as a model for bone studies. The tibia of the dog is large enough to allow large (>5 mm) defects to be created and studied without compromising the ability of the animal to ambulate without inducing fractures secondary to induction of defects in the bones.

Ten adult male and female beagle dogs (6.0–15.0 kg) received the same treatment; Defects were created in the lateral surface of the tibial crest cortex (8 mm or 10 mm) in each tibia. PCA calcium phosphate was placed in the defect in one tibia and the other tibia served as a control.

An incision was made over the proximal tibia. The soft tissue was deflected away and the bone was exposed. Using an 8 mm trephine in a low speed dental handpiece with irrigation (0.9% physiologic saline) as needed, the bony disk was dissected free and the site was prepared for implantation. The inventive calcium phosphate material (solid or paste) was placed into the defect. The soft tissues were then closed in layers. One to three samples per animal were performed using this method. The animals were allowed to heal for scheduled periods of time.

Animals were assessed by clinical observations, radiographs, and microscopy of the defect sites at 0, 2, 4, and 8 weeks. Specifically, tibia radiographs were taken every 2 weeks throughout the study. The radiographs were used to determine the duration of the study. Approximately at the end of every 2 weeks, 2 animals were sacrificed and the test sites were removed for histology. The implantation sites were prepared as undecalcified and decalcified sections.

Two dogs were used as pilot animals and did not receive and PCA material. In these pilot animals, some healing was observed radiographically at 2 weeks. By 6–8 weeks, the defect was completely healed. The size of dog defects was determined to be optimal at 1 cm. In the remaining 8 dogs, control defects healed within 6 weeks; treated defects healed in 2 to 4 weeks. The quality of the bone in the control defects was thin trabecular bone; in the treated defects, the bone was thick trabecular to cortical type bone. Thus, the treated defects healed approximately 2 weeks faster than did untreated defects, and healed with better bone thickness.

Figure 11:
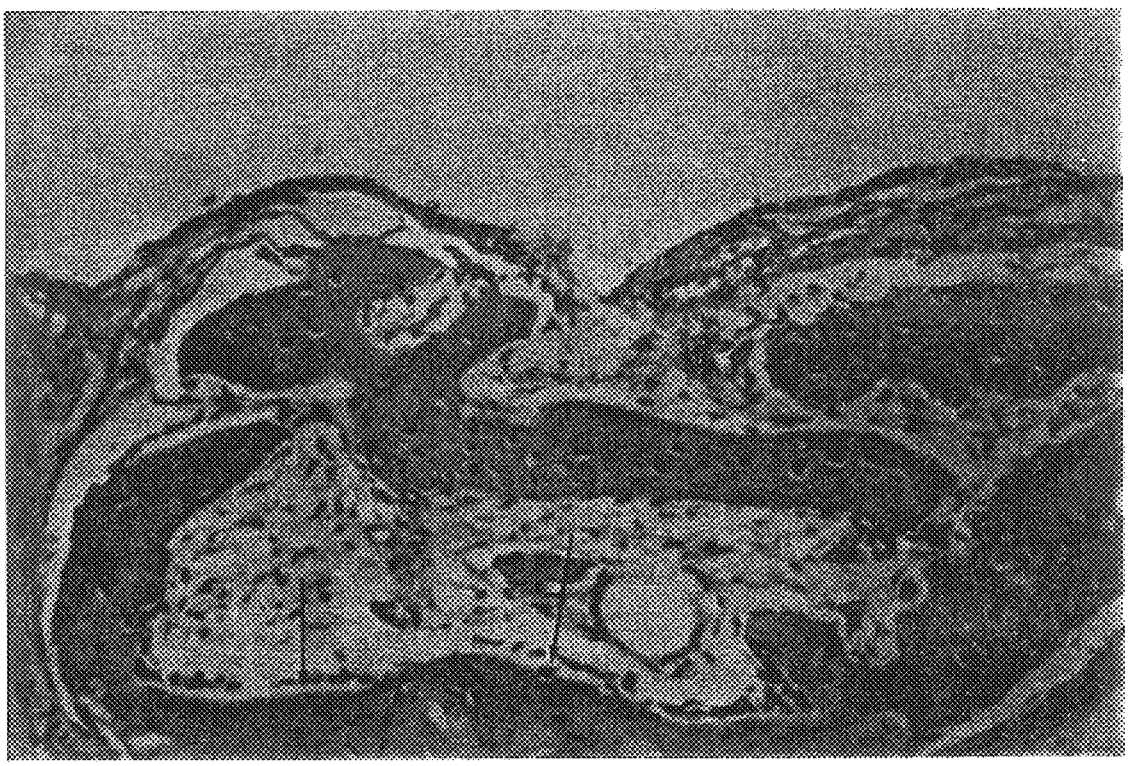
FIG. 11 is a photomicrograph of canine trabecular bone grown into a defect 8 weeks after surgery treated with the drug delivery vehicle of the present invention. (Magnification 10×; decalcified; hematoxylin and eosin).

FIG. 11 shows a highly magnified (10×) photograph of canine trabecular bone growth into a defect site treated with the PCA material of the invention 8 weeks after surgery. The small arrows denote osteoblast—like cells lining the bone spicules and are indicative of enhanced cellular activity.

Figure 12:
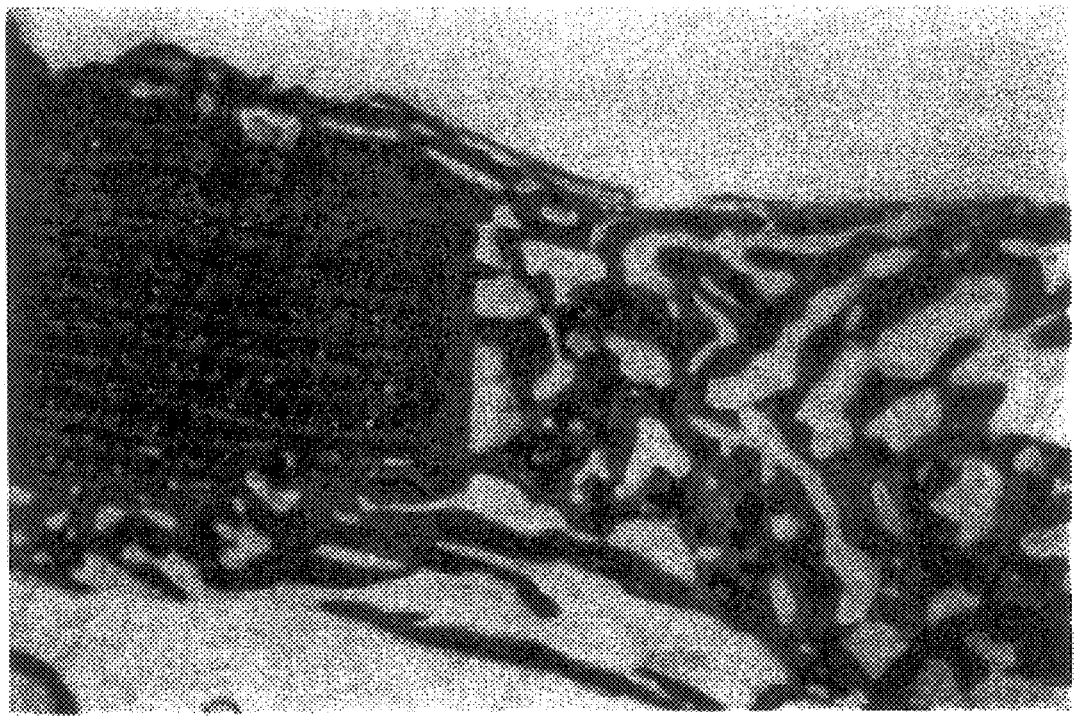
FIG. 12 is a photomicrograph of a canine cortical bone defect 4 weeks after surgery that was treated with the drug delivery vehicle of the present invention. (Magnification 4×; undecalcified, Light Green Basic Fuchsin).

FIG. 12 shows a photomicrograph of a canine cortical bone defect treated with the PCA material of the invention. The large arrows indicate one edge of the defect. The new bone growth is to the right of the defect; at 4 weeks after surgery, this growth is thick trabecular bone.

Example 18

Implantation and Resorption of Drug Delivery Vehicle in a Bony Site

The purpose of this study was to assay resorption and ossification of the PCA calcium phosphate of the invention, and to establish parameters for screening test PCA calcium phosphate materials.

Eighteen adult (>3 month old) NZW male rabbits were used in these studies. After obtaining adequate anesthesia (e.g., ketamine/xylazine to effect), using aseptic technique, an incision was made over the proximal tibia. The soft tissue was deflected away and the bone was exposed. Using an approximately 5 mm trephine in a low speed dental handpiece with irrigation (0.9% physiologic saline) as needed, the bony disk was dissected free and the site was prepared for implantation. The inventive PCA calcium phosphate material (solid, granules or paste) was placed into the defect. The soft tissues were then closed in layers.

Clinical observations of the animals general health and well-being, with special regard to ambulation, were performed weekly and in more detail at the time of the bi-weedly radiographs. Radiographs of the tibiae were made at scheduled intervals including after surgery and at the time of necropsy.

The implantation sites were prepared as hematoxylin & eosin, Masson's trichrome decalcified samples and as undecalcified slides.

Findings and clinical observations were associated with surgery and were not associated with the PCA calcium phosphate implants. Postsurgical clinical observations were within the range of anticipated fmdings for surgery-related trauma. Radiographs were taken immediately postsurgery and at each scheduled sacrifice timepoint.

Immediately after surgery, all bone defect sites were distinct; implants appeared to have the same radiodensity as bone. At 2 weeks postsurgery, control defects had distinct sites and implant sites were less distinct and blended into surrounding bone; similar fmdings were observed at 4 weeks. At 7 weeks, all sites appeared similar with increased radiodensity. Grossly, defect sites at 2 weeks were visible clearly in control and treated animals. At 4 weeks and greater, the implant or control sites could not be grossly ascertained.

Radiographic fmdings indicated little change in the control animals until week 7; animals treated with inventive PCA material had increasing radiodensity in the defect over time. Defects in control animals had some new bone ingrowth, predominantly of the thin trabecular type, within 4–7 weeks. Defects in treated animals had bone ingrowth as early as 2 weeks and by 7 weeks were filled with new bone. Microscopic fmdings are consistent with enhanced bone replacement with PCA calcium phosphate implants. Taken together, this study shows that 5 mm defects in rabbit tibia heal or have new bone growth in control animals by 7 weeks and in animals treated with the inventive PCA material by 4 weeks. Also, this rabbit unicortical 5 mm critical sized defect model is useful to analyze test articles for there resorptive and ossificative properties.

Figure 13A:
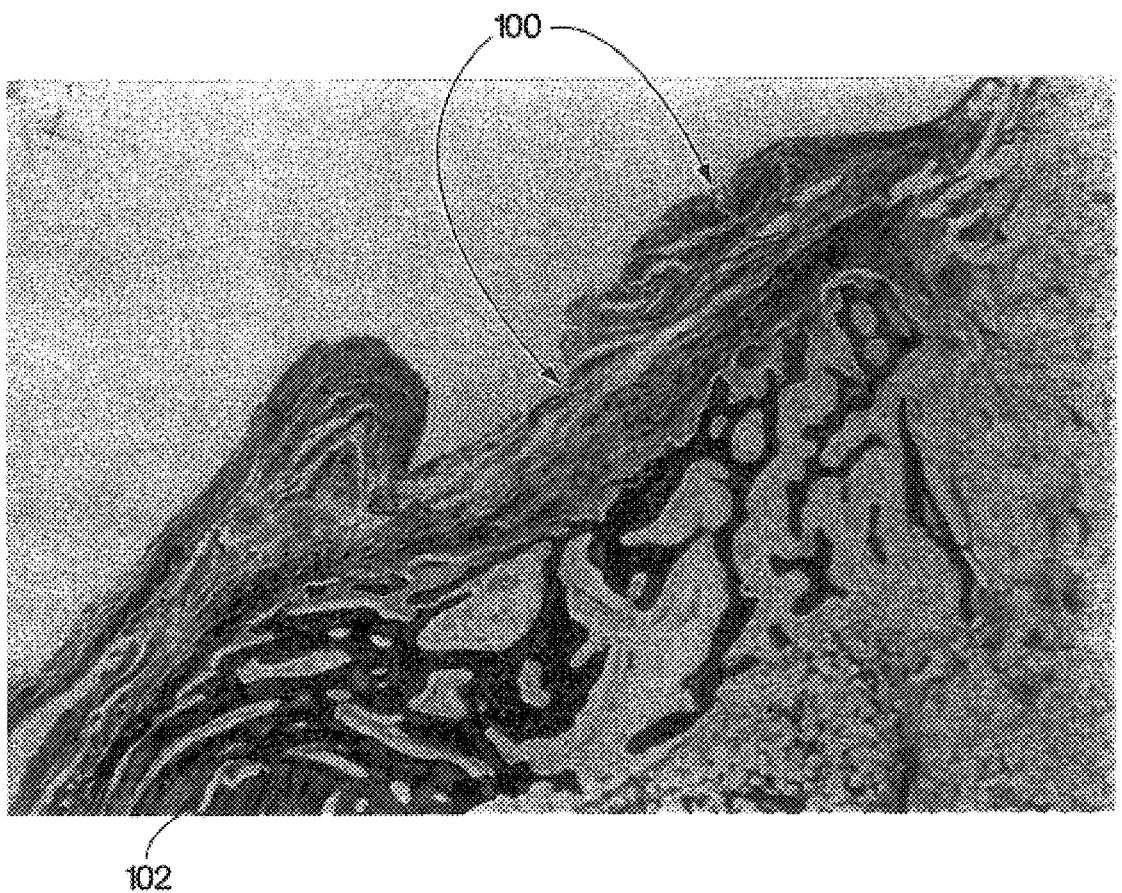
FIG. 13 presents photomicrographs of untreated (FIG. 13a) and treated (FIG. 13b) rabbit tibia defects 4 weeks after surgery (Magnification 4×; decalcified; Masson's Trichrome).
Figure 13B:
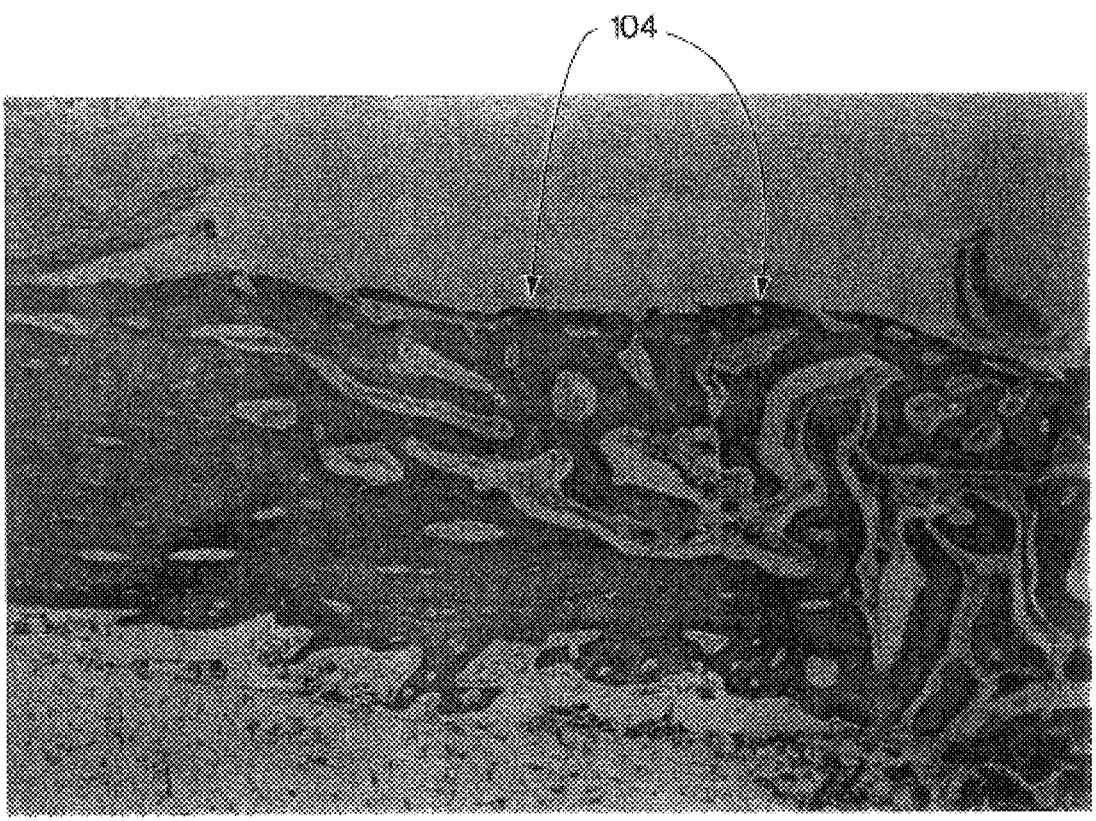

FIG. 13 shows photomicrographs of untreated (FIG. 13a) and treated (13b) rabbit tibia defects 4 weeks after surgery. The large arrow indicates the edge of the defect. In FIG. 13a, small arrows 100 denote an abundance of fibrous connective tissue on the defect site. The large arrowhead 102 points to new trabecular bone in the defect. In FIG. 13b, the two small arrows 104 demarcate the thick trabecular bone growth in the defect site.

Example 19

Variation of Resorption Rates of Synthetic PCA Materials by Varying Particle Size PCA precursor material is prepared according to Example 5. Two precursor mixes are prepared, sample A corresponding to sample 6 and sample B to a 2:4:3:1 mix of samples 1,2,3,&4. Hydrated precursor pastes of the two samples are tested in rodents in the subcutaneous test of Example 15. Resorption is monitored at various time points.

Example 20

Incorporation of a Biologically Active Agent into a Drug Delivery Device and Preservation of in vitro Stability This example demonstrates the incorporation of a protein into a delivery vehicle of the present invention in a manner that preserves the protein's in vitro stability.

Bovine pancreatic trypsin is prepared in phosphate buffered saline at a concentration of 100 mg/ml. 0.8 ml of this solution is added to 1 g of a 1:1 mixture of activated ACP and DCPD as described in Example 17, sample B. The mixture is formed into a ball and hardened in a moist environment at 37° C. for 30 minutes. The hardened ball is then lyophilized overnight and subsequently it is ground by and with a mortar and pestle. The powder formed this way is mixed with 1 ml of water and applied to wells in a casein assay plate. The clearance of the cloudy casein in a ring around the well is compared to the clearance observed in a well similarly loaded with a lyophilized PCA sample continuing heat inactivated tripsin.

Example 21

Incorporation of a Biologically Active Agent into a Drug Delivery Device and Preservation of in vivo Stability This example demonstrates the incorporation of a protein into a delivery vehicle of the present invention in a manner that preserves the protein's in vivo activity.

200 mg/ml Beta galactosidase (Worthington LS004093) is prepared in phosphate buffered saline pH 7.0. 0.8 ml of this solution is added to 1 g of a 1:1 mixture of activated ACP and DCPD (prepared as described in example 17, sample B.) and mixed into a putty. The formable PCA is then prepared in a ball and implanted subcutaneously in a rat. Two weeks later the PCA ball is removed, lyophilized and ground with a mortar and pestle. The powder is then assayed for beta galactosidase activity, for example using a liquid assay such as that described by Miller (*Experiments in Molecular Genetics*, Cold Spring Harbor Laboratory Press, Cold Spring Harbor, N.Y., 1972).

Example 22

Delivery of an Antibiotic

This example demonstrates use of the delivery vehicle of the present invention to deliver antibiotic in a dental application.

100 mg/ml gentamycin is prepared in phosphate buffered saline pH 7.0. 0.8 ml of this solution is added to 1 g of a 1:1 mixture of activated ACP and DCPD (prepared as described in Example 17, sample B.) and mixed into a putty. The formable PCA is then prepared in a ball and implanted subcutaneously in a rat. Two weeks later the PCA ball is removed, lyophilized and ground with a mortar and pestle. The powder is then assayed for bactericidal activity using a USP bacteriacidal/bacterialstasis zone of inhibition test.

Example 23

Delivery of a Vaccine

This example demonstrates use of the delivery vehicle of the present invention to deliver a vaccine.

Keyhole limpet hemocyanin is prepared at a concentration of 0.5 mg/ml in phosphate buffered saline pH 7.0. 0.8 ml of this solution is added to 1 g of a 1:1 mixture of activated ACP and DCPD (prepared as described in Example 17, sample B.) and mixed into a putty. The formable PCA is then prepared in a ball and implanted subcutaneously in a rat. The process is repeated on a monthly basis for four months. Blood samples are taken on a regular basis and anti-Keyhole limpet hemocyanin antibody titers are determined by EUSA.

Example 24

Delivery of a Nucleic Acid

This example demonstrates use of the delivery vehicle of the present invention for intramuscular delivery of a nucleic acid for the purpose of cell transfection. This method may also be used to incorporate DNA into tissues other than muscle.

pUC19 plasmid DNA is prepared in EDTA TRIS pH 7.4 at 2 mg/ml. 0.8 ml of this solution is added to 1 g of a 1:1 mixture of activated ACP and DCPD (prepared as described in example 17, sample B.) and mixed into a putty. The formable PCA is then prepared in a ball and implanted intramuscularly in a rat. After 4 weeks the muscle at the implant site is dissected and histologically stained for the presence of the B galactosidase gene product.

Example 25

Implantation and Resorption of Drug Delivery Device for Treatment of Parkinson's Disease This example demonstrates use of the delivery vehicle of the prevent invention to deliver a drug for the treatment of Parldnson's Disease.

Primates are made hemi-parkinsonian with MPTP and evaluated behaviorally as described in Kordower et al., *Cell Transplantation* 14:155–171, 1995.

200 mg/ml GDNF is prepared in phosphate buffered saline pH 7.0. 0.8 ml of this solution is added to 1 g of a 1:1 mixture of activated ACP and DCPD (prepared as described in Example 17, sample B.) and mixed into a putty. The hydrated PCA precursor is then shaped into 3 cylinders each approximately 1 mm×1 cm and hardened in a moist environment at 37° C.

The cylinders are then placed in the lateral ventricles on the lesioned side of the experimental animals and the primates are continued to be behaviorally evaluated. After two months the animals are sacrificed and neurons of the substantia nigra and striatum are analyzed for tyrosine hydroxylase activity.

Other Embodiments

It will be understood that the foregoing is merely a description of certain preferred embodiments of the invention and is not intended to be limiting thereof. The following claims cover all of the generic and specific features of the invention herein described in the text and accompanying drawings.

What is claimed is:

1. A vehicle for delivering a biologically active agent, comprising:

an amorphous calcium phosphate (ACP), an acidic calcium phosphate and an aqueous solution in an amount to provide a paste of formable or injectable consistency, the paste being capable of hardening in association with an endothermic reaction; and a biologically active agent contained in or on the paste.

2. The vehicle of claim 1, wherein the acidic calcium phosphate is selected so that, in combination with the ACP, a Ca/P ratio within the range of about 1.1–1.9 is obtained.

3. The delivery vehicle of claim 1, wherein the acidic calcium phosphate is selected so that, in combination with the ACP, a Ca/P ratio within the range of about 1.2 to 1.68 is obtained.

4. The delivery vehicle of claim 1, wherein the acidic calcium is selected from the group consisting of dicalcium phosphate dihydrate, calcium metaphosphate, heptacalcium phosphate, poorly crystalline hydroxyapatite, calcium pyrophosphates, octacalcium phosphate, and tricalcium phosphates.

5. The delivery vehicle of claim 1, wherein the acidic calcium phosphate has a pH in the range of about 5–7.

6. The vehicle of claim 1, wherein the biologically active agent is selected from the group consisting of proteins, polypeptides, polynucleotides, nucleoproteins, polysaccharides, glycolproteins, and lipoproteins.

7. The vehicle of claim 1, wherein the biologically active agent is selected from the group consisting of anti-AIDS substances, anti-cancer substances, antibiotics, ACE inhibitors, antigens, adrenergic antagonists, antacids, immunosuppressants, anti-viral substances, enzyme inhibitors, neurotoxins, opioids, hypnotics, antihistamines, lubricants, tranquilizers, anti-convulsions, muscle relaxants, anti-Parkinson substances, anti-spasmodics, muscle contractants, anti-diarrheals, anti-emetics, laxatives, diuretics, miotics, anti-cholinergics, anti-glaucoma compounds, anti-parasite compounds, anti-protozoal compounds, anti-hypertensives, analgesics, anti-pyretic, anti-inflammatory agents, anti-histamines, anti-tussive agents, anti-vertigo, antinertigic, anti-motion sickness medications, local anesthetics, ophthalmics, prostaglandins, anti-depressants, anti-psychotic substances, anti-emetics, imaging agents, specific targeting agents, trophic factors, growth factors, neurotransmitters, cell response modifiers, and vaccines.

8. The vehicle of claim 1, wherein the paste is characterized by a tendency to harden at 22° C. after time a longer than one hour.

9. The vehicle of claim 1, wherein the paste is characterized by a tendency to harden at 37° C. after time shorter than one hour.

10. The vehicle of claim 1, wherein the paste is characterized by tendency to harden at 22° C. after about 10–30 minutes.

11. The vehicle of claim 1, further comprising an additional material selected to change the physical parameter of the vehicle, which physical parameter is selected from the group consisting of strength, resorption time, adherence, injectability, frictional characteristics, and release kinetics.

12. The vehicle claim 1, wherein the paste further comprises a calcium source that participates in the hardening of the paste and is incorporated into the hardened calcium phosphate.

13. The vehicle of claim 1, wherein the paste further comprises a phosphate source that participates in the hardening of the paste and is incorporated into the hardened calcium phosphate.

14. The vehicle of claim 1, wherein the paste comprises an acidic calcium phosphate selected to provide appropriate stoichiometry for reaction with the ACP to produce a poorly crystalline apatitic calcium phosphate.

15. The vehicle of claim 1, wherein the acidic calcium phosphate comprises dicalcium phosphate dihydrate (DCPD).

16. The vehicle of claim 1, wherein the acidic calcium phosphate comprises stoichiometric hydroxyapatite.

17. The vehicle of claim 1, wherein the paste further comprises a promoter selected from the group consisting of $Al_2O_3$, mica, glass, and sand.

18. The vehicle of claim 1 wherein hardening of the paste is promoted by heating the paste.

19. The vehicle of claim 1, wherein the paste is formed by mixing the ACP, the acidic calcium phosphate, and a biologically active agent together in a buffered solution selected for its compatibility with the biologically active agent.

20. The vehicle of claim 1, wherein the paste is formed by mixing the amorphous calcium phosphate and the acidic calcium phosphate together in an aqueous solution, so that a paste is formed;

allowing the mixture to harden in an endothermic process; and applying the biologically active agent to the hardened calcium phosphate.

21. A method of producing a vehicle for delivering a biologically active agent, the method comprising the steps of:

reacting an amorphous calcium phosphate with an acidic calcium phosphate in a proportion to form a poorly crystalline apatitic calcium phosphate, the reaction being performed in an aqueous medium and in the presence of a biologically active agent, the aqueous medium and the reaction conditions being selected to preserve activity of the biologically active agent, so that the biologically active agent is incorporated into or onto the poorly crystalline apatitic calcium phosphate.

22. A method of producing a vehicle for delivering a biologically active agent, the method comprising the steps of:

mixing, in any order, an amorphous calcium phosphate (ACP); a biologically active material, an acidic calcium phosphate, and a buffered aqueous solution selected for compatibility with the biologically active agent; and allowing the mixture to harden in association with an endothermic reaction after mixing.

23. The method of claim 21, wherein the formation of a poorly crystalline calcium apatite is associated with hardening.

24. The method of claim 21 or 22, wherein the acidic calcium phosphate is selected so that, in combination with the ACP, a Ca/P ratio within the range of about 1.1–1.9 is obtained.

25. The method of claim 21 or 22, wherein the acidic calcium phosphate is selected so that, in combination with the ACP, a Ca/P ratio within the range of about 1.2 to 1.68 is obtained.

26. The method of claim 21 or 22, wherein the acidic calcium is selected from the group consisting of dicalcium phosphate dihydrate, calcium metaphosphate, heptacalcium phosphate, poorly crystalline hydroxyapatite, calcium pyrophosphates, octacalcium phosphate, and tricalcium phosphates.

27. The method of claim 21 or 22, wherein the acidic calcium phosphate has a pH in the range of about 5–7.

28. The method of claim 21 or 22, wherein the biologically active agent is selected from the group consisting of proteins, polypeptides, polynucleotides, nucleoproteins, polysaccharides, glycolproteins, and lipoproteins.

29. The method of claim 22 or 23, wherein the biologically active agent is selected from the group consisting of anti-AIDS substances, anti-cancer substances, antibiotics, ACE inhibitors, antigens, adrenergic antagonists, antacids, immunosuppressants, anti-viral substances, enzyme inhibitors, neurotoxins, opioids, hypnotics, antihistamines, lubricants, tranquilizers, anti-convulsions, muscle relaxants, anti-Parkinson substances, anti-spasmodics, muscle contractants, anti-diarrheals, anti-emetics, laxatives, diuretics, miotics, anti-cholinergics, anti-glaucoma compounds, anti-parasite compounds, anti-protozoal compounds, anti-hypertensives, analgesics, anti-pyretic, anti-inflammatory agents, anti-histamines, anti-tussive agents, anti-vertigo, antinertigic, anti-motion sickness medications, local anesthetics, ophthalmics, prostaglandins, anti-depressants, anti-psychotic substances, anti-emetics, imaging agents, specific targeting agents, trophic factors, growth factors, neurotransmitters, cell response modifiers, and vaccines.

30. The method of claim 22 or 23, wherein the mixture hardens at 22° C. after time a longer than one hour.

31. The method of claim 22 or 23, wherein the mixture hardens at 37° C. after time shorter than one hour.

32. The method of claim 22 or 23, wherein the mixture hardens at 22° C. after about 10–30 minutes.

33. The method of claim 22 or 23, further including step of forming the hardened calcium phosphate into a predetermined shape.

34. The method of claim 22 or 23, further, including step of implanting the hardened calcium phosphate into a subject.

35. The method of claim 34 wherein the step of the implanting comprises implanting in a site selected from the group consisting of bone, muscle, the spinal cord, the central nervous system, the interperitoneal cavity, a subcutaneous location, and the vitreous and aqueous humor of the eye.

36. A method of delivering a biologically active agent, comprising:
    providing a paste comprising an amorphous calcium phosphate (ACP), an acidic calcium phosphate and a biologically active agent in an aqueous solution in an amount to provide a formable or injectable consistency;
    applying the paste to a site requiring a biologically active agent; and
    allowing the paste to harden at the site in association with an endothermic reaction.

37. The method of claim 36, comprising:
    forming the paste into a predetermined shape and applying the shaped paste to the site.

38. The method of claim 36, wherein the step of applying the paste comprises injecting the paste into the site.

39. The method of claim 36, wherein the site is selected from the group consisting of bone, muscle, the spinal cord, the central nervous system, the interperitoneal cavity, a subcutaneous location, and the vitreous and aqueous humor of the eye.

40. The method of claim 36, wherein the acidic calcium phosphate is selected so that, in combination with the ACP, a Ca/P ratio within the range of about 1.1–1.9 is obtained.

41. The method of claim 36, wherein the acidic calcium phosphate is selected so that, in combination with the ACP, a Ca/P ratio within the range of about 1.2 to 1.68 is obtained.

42. The method of claim 36, wherein the acidic calcium is selected from the group consisting of dicalcium phosphate phosphate dihydrate, calcium metaphosphate, heptacalcium phosphate, poorly crystalline hydroxyapatite, calcium pyrophosphates, octacalcium phosphate, and tricalcium phosphates.

43. The method of claim 36, wherein the acidic calcium phosphate has a pH in the range of about 5–7.

44. The method of claim 36, wherein the biologically active agent is selected from the group consisting of proteins, polypeptides, polynucleotides, nucleoproteins, polysaccharides, glycolproteins, and lipoproteins.

45. The method of claim 36, wherein the biologically active agent is selected from the group consisting of anti-AIDS substances, anti-cancer substances, antibiotics, ACE inhibitors, antigens, adrenergic antagonists, antacids, immunosuppressants, anti-viral substances, enzyme inhibitors, neurotoxins, opioids, hypnotics, antihistamines, lubricants, tranquilizers, anti-convulsions, muscle relaxants, anti-Parkinson substances, anti-spasmodics, muscle contractants, anti-diarrheals, anti-emetics, laxatives, diuretics, miotics, anti-cholinergics, anti-glaucoma compounds, anti-parasite compounds, anti-protozoal compounds, anti-hypertensives, analgesics, anti-pyretic, anti-inflammatory agents, anti-histamines, anti-tussive agents, anti-vertigo, antinertigic, anti-motion sickness medications, local anesthetics, ophthalmics, prostaglandins, anti-depressants, anti-psychotic substances, anti-emetics, imaging agents, specific targeting agents, trophic factors, growth factors, neurotransmitters, cell response modifiers, and vaccines.

46. The method of claim 36, wherein the mixture hardens at 22° C. after time a longer than one hour.

47. The method of claim 36, wherein the mixture hardens at 37° C. after time shorter than one hour.

48. The method of claim 36, wherein the mixture hardens at 22° C. after about 16–30 minutes.

49. The method of claim 36, wherein the site requiring a biologically active agent is selected from the group consisting of bone, muscle, the spinal cord, the central nervous system, the interperitoneal cavity, a subcutaneous location, and the vitreous and aqueous humor of the eye.

50. The method of claim 36, wherein the hardened paste is bioresorbable.

51. The method of claim 50, wherein at least about 80% of the PCA calcium phosphate is resorbed within one year.

52. The method of claim 50, wherein at least one gram of PCA calcium phosphate, at least about 80% of the PCA calcium phosphate is resorbed within nine months.

53. The method of claim 50, wherein at least about 80% of the PCA calcium phosphate is resorbed within six months.

54. The method of claim 50, wherein at least about 80% of the PCA calcium phosphate is resorbed within three months.

55. The vehicle of claim 50, wherein at least about 80% of the PCA calcium phosphate is resorbed within one month.

56. A vehicle for delivering a biologically active agent comprising:
    a calcium phosphate source comprising:
    at least about 50 wt % amorphous calcium phosphate (ACP) and an acidic calcium phosphate; and
    an aqueous solution in an amount to provide a paste of formable or injectable consistency with the calcium phosphate source, the paste being capable of hardening in association with an endothermic reaction; and
    a biologically active agent contained in or on the paste.

57. A vehicle for delivering a biologically active agent comprising:
    a calcium phosphate source consisting essentially of an amorphous calcium phosphate (ACP) and an acidic calcium phosphate;
    an aqueous solution in an amount to provide a paste of formable or injectable consistency with the calcium phosphate source, the paste being capable of hardening in association with an endothermic reaction; and
    a biologically active agent contained in or on the paste.

* * * * *

UNITED STATES PATENT AND TRADEMARK OFFICE
CERTIFICATE OF CORRECTION

PATENT NO.    : 6,541,037 B1
DATED         : April 1, 2003
INVENTOR(S)   : Lee et al.

It is certified that error appears in the above-identified patent and that said Letters Patent is hereby corrected as shown below:

Column 37,
Line 52, please delete "after time a longer" and replace it with -- after a time longer --.
Line 55, please delete "after time shorter" and replace it with -- after a time shorter --.
Line 58, please delete "by tendency to harden" and replace it with -- by a tendency to harden --.
Line 64, please delete "The vehicle claim 1" and replace it with -- The vehicle of claim 1 --.

Column 38,
Line 15, please delete "The vehicle of claim 1" and replace it with -- The vehicle of claim 1, --.

Column 39,
Line 22, please delete "after time a longer" and replace it with -- after a time longer --.
Line 29, please delete "further, including step" and replace it with -- further including step --.
Line 31, please delete "The method of claim 34" and replace it with -- The method of claim 34, --.

Column 40,
Line 24, please delete "after time a longer" and replace it with -- after a time longer --.
Line 27, please delete "after about 16-30 minutes" and replace it with -- after about 10-30 minutes --.

Signed and Sealed this

Eleventh Day of November, 2003

JAMES E. ROGAN
*Director of the United States Patent and Trademark Office*